(12) United States Patent
Fukuda

(10) Patent No.: US 9,949,706 B2
(45) Date of Patent: Apr. 24, 2018

(54) IMAGE-PROCESSING DEVICE, RADIOGRAPHIC IMAGING SYSTEM, IMAGE-PROCESSING PROGRAM, AND IMAGE-PROCESSING METHOD

(71) Applicant: FUJIFILM CORPORATION, Minato-ku, Tokyo (JP)

(72) Inventor: Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 91 days.

(21) Appl. No.: 15/080,594

(22) Filed: Mar. 25, 2016

(65) Prior Publication Data

US 2016/0206268 A1 Jul. 21, 2016

Related U.S. Application Data

(63) Continuation of application No. PCT/JP2014/075723, filed on Sep. 26, 2014.

(30) Foreign Application Priority Data

Sep. 30, 2013 (JP) .................................. 2013-205479

(51) Int. Cl.
    *G06K 9/00* (2006.01)
    *A61B 6/00* (2006.01)
    *A61B 6/02* (2006.01)
    *A61B 6/03* (2006.01)

(52) U.S. Cl.
    CPC ............ *A61B 6/5235* (2013.01); *A61B 6/025* (2013.01); *A61B 6/032* (2013.01); *A61B 6/463* (2013.01); *A61B 6/502* (2013.01); *A61B 6/5205* (2013.01); *A61B 6/5211* (2013.01); *A61B 6/5258* (2013.01)

(58) Field of Classification Search
    None
    See application file for complete search history.

(56) References Cited

U.S. PATENT DOCUMENTS

| | | | | |
|---|---|---|---|---|
| 8,600,137 B2* | 12/2013 | Bruder | ................... | A61B 6/032 382/131 |
| 9,008,262 B2* | 4/2015 | Nakanishi | .............. | A61B 6/032 378/19 |
| 9,311,695 B2* | 4/2016 | Takahashi | ............ | A61B 6/5205 |
| 2010/0135558 A1 | 6/2010 | Ruth et al. | | |

* cited by examiner

*Primary Examiner* — Soo Park
(74) *Attorney, Agent, or Firm* — Solaris Intellectual Property Group, PLLC

(57) ABSTRACT

Provided are an image processing device, a radiography system, an image processing program, and an image processing method which can generate a tomographic image used for radiographic interpretation and a tomographic image suitable for generating a composite two-dimensional image from a projection image obtained by tomosynthesis imaging. A frequency processing unit and a tomographic image generation unit generate a first tomographic image which is emphasized according to a spatial frequency and is used for radiographic interpretation, on the basis of the projection images obtained by tomosynthesis imaging, and generate a second tomographic image which is emphasized according to the spatial frequency and on which the degree of emphasis is different from the degree of emphasis on the first tomographic image, on the basis of the projection image. A two-dimensional image generation unit combines a plurality of second tomographic images to generate a composite two-dimensional image.

18 Claims, 18 Drawing Sheets

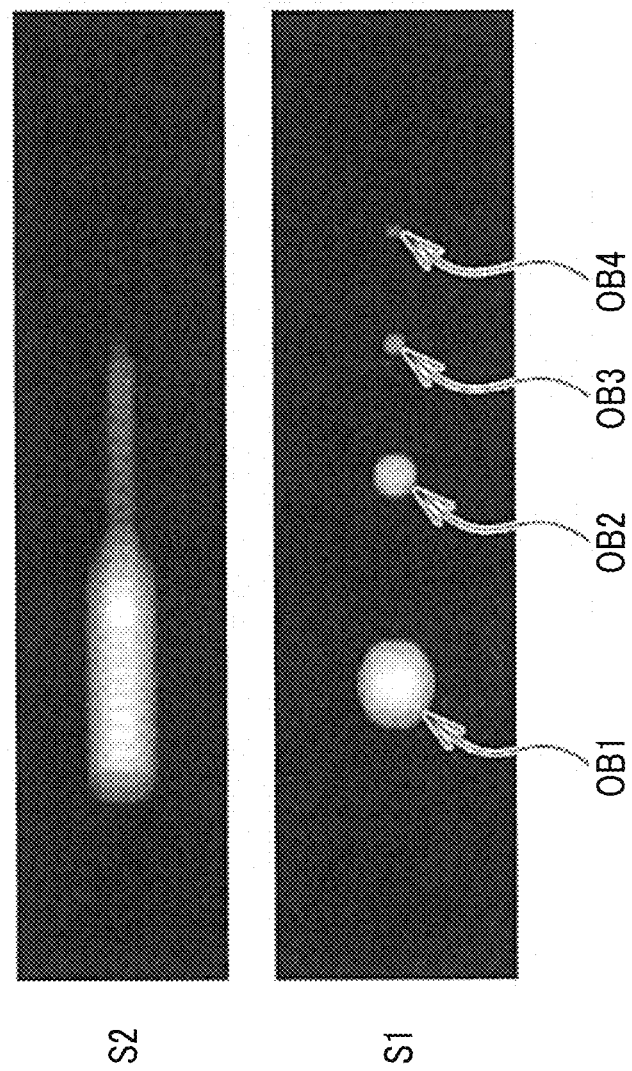

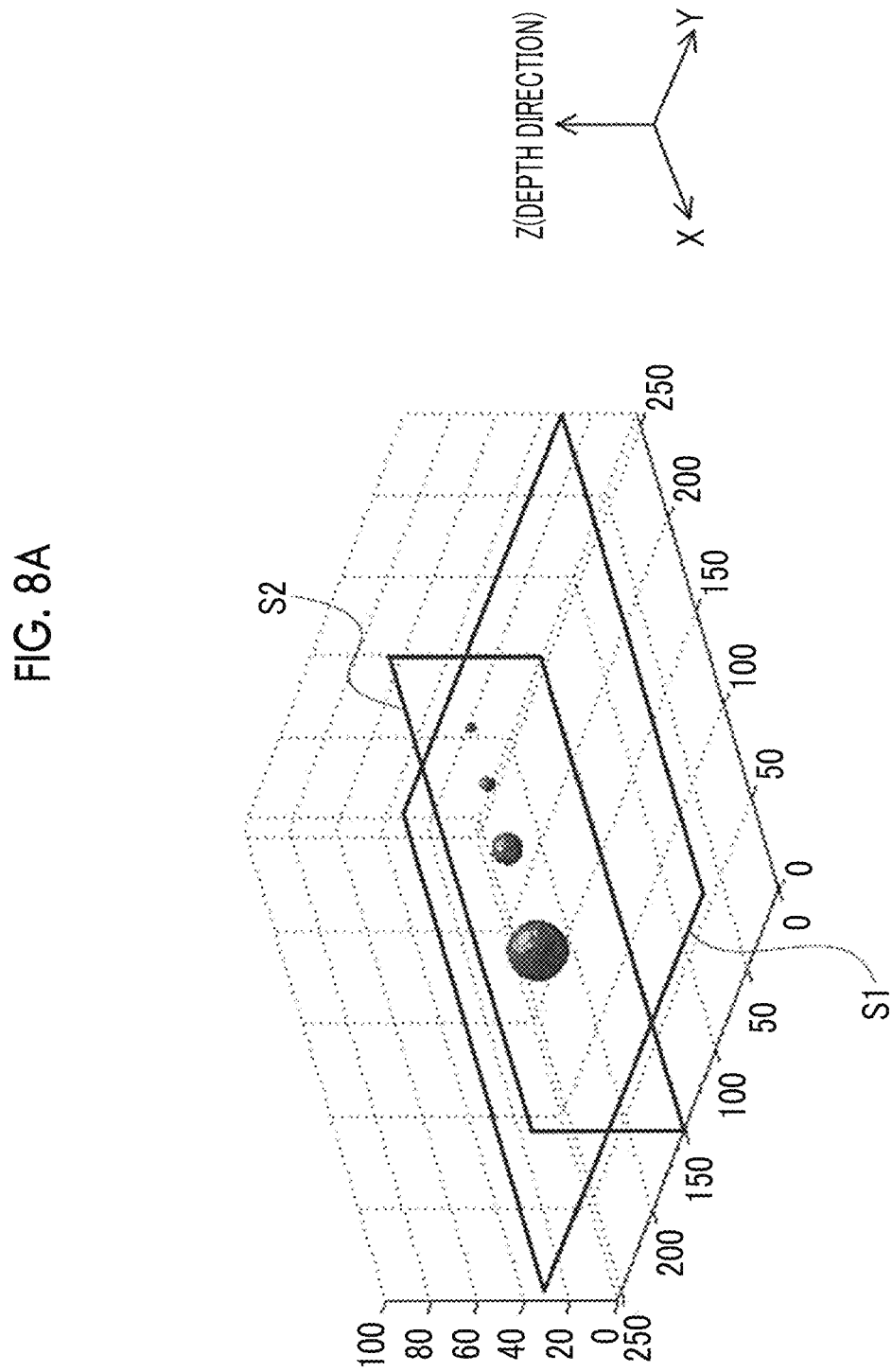

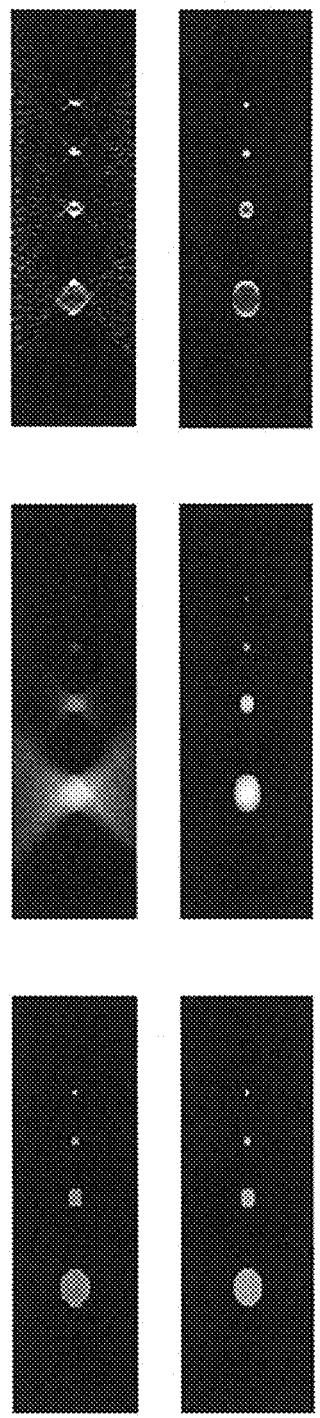

IMAGE-PROCESSING DEVICE, RADIOGRAPHIC IMAGING SYSTEM, IMAGE-PROCESSING PROGRAM, AND IMAGE-PROCESSING METHOD

CROSS-REFERENCE TO RELATED APPLICATIONS

This application is a continuation application of International Application No. PCT/JP2014/075723, filed Sep. 26, 2014, the disclosure of which is incorporated herein by reference in its entirety. Further, this application claims priority from Japanese Patent Application No. 2013-205479 filed Sep. 30, 2013, the disclosure of which is incorporated herein by reference in its entirety.

BACKGROUND OF THE INVENTION

1. Field of the Invention

The present invention relates to an image processing device, a radiography system, an image processing program, and an image processing method, and more particularly, to an image processing device, a radiography system, an image processing program, and an image processing method which generate a tomographic image from projection images that are captured by emitting radiation at different incident angles.

2. Description of the Related Art

A radiography apparatus is known which captures radiological images for medical diagnosis. An example of this type of radiography apparatus is a mammography apparatus which captures an image of the breast of a subject for the early detection of breast cancer. In addition, in mammography, a tomosynthesis imaging technique is known which irradiates the breast of the subject with radiation at different angles to capture images of the breast. The tomosynthesis imaging technique irradiates a subject that is positioned between a radiation detector and a radiation emitting unit and of which the tomographic image is to be generated with radiation at different incident angles (hereinafter, simply referred to as "incident angles") with respect to a direction normal to a tomographic plane of the tomographic image in a predetermined range while moving the radiation emitting unit, captures images of the subject at different incident angles, and reconstructs a plurality of captured radiological images (hereinafter, referred to as "projection images") to generate tomographic images at a predetermined slice interval.

In mammography diagnosis, tomosynthesis imaging has come into widespread use. However, in many cases, tomographic images obtained by the tomosynthesis imaging are used to supplement radiological images obtained by general two-dimensional imaging which irradiates a subject with radiation at a fixed position, without moving a radiation emitting unit, and captures images of the subject. The reason for this is that the radiological image obtained by general two-dimensional imaging has concentration that a doctor is accustomed to seeing and is different from that of the tomographic image and the doctor can check the entire radiological image at one time.

For this reason, in many cases, both the two-dimensional imaging and the tomosynthesis imaging are performed and diagnosis is performed using a combination of the radiological image obtained by the two-dimensional imaging and the tomographic image obtained by the tomosynthesis imaging.

However, if an image corresponding to the radiological image obtained by the general two-dimensional imaging can be obtained by only the tomosynthesis imaging, it is possible to significantly reduce a radiation dose and an imaging time during imaging, which is preferable.

As a technique which generates an image corresponding to the radiological image obtained by the general two-dimensional imaging from the tomographic image obtained by the tomosynthesis imaging, US2010/0135558A discloses a method which captures a plurality of X-ray tomosynthesis projection images of the breast of a patient and combines at least one sub-set of a plurality of X-ray tomosynthesis projection images to synthesize two-dimensional mammograms, using at least one of an algebraic method and a maximum intensity projection method.

Hereinafter, a two-dimensional image, such as a two-dimensional mammogram generated by combining a plurality of tomographic images, is referred to as a "composite two-dimensional image".

SUMMARY OF THE INVENTION

However, in the tomosynthesis imaging, the incident angle of radiation during irradiation is limited. Therefore, for example, even if projection images are simply superimposed to reconstruct tomographic images using a back projection method, a virtual image (hereinafter, referred to as an "artifact") of an object which is not originally present may appear in a region in which the object is not originally present. In this case, when the virtual image is too conspicuous, it is difficult to see the object of interest. In addition, the same problems as described above occur in a case in which the tomographic image is reconstructed by other methods.

In contrast, in order to solve the above-mentioned problems, the following method is considered: a filtered back projection (FBP) method, which is a representative example of a computed tomography (CT) reconstruction method, is applied to reconstruct a tomographic image from a projection image, which has been uniformly subjected to a filtering process using a so-called ramp filter (hereinafter, referred to as a "first filter") that attenuates a low frequency component in a spatial frequency domain as illustrated in FIG. 15, using back projection.

In this case, the virtual image in the depth direction is reduced in intensity a little. However, in the case of tomosynthesis imaging, when filtering process is uniformly performed, the concentration of a subject image in the tomographic image is different from the concentration of the projection image. In this case, when the tomographic images are combined to generate a composite two-dimensional image, the concentration of a subject image in the composite two-dimensional image is also different from the concentration of the projection image.

As a method for reconstructing a tomographic image from a projection image, for example, a method is known which reconstructs a tomographic image from a projection image, which has been uniformly subjected to a filtering process using a high frequency emphasis filter (hereinafter, referred to as, a "second filter") that does not attenuate a low frequency component, as illustrated in FIG. 15, using back projection.

In this case, the concentration of the subject image in the tomographic image can be close to the concentration of the projection image. However, since the low frequency component is not attenuated, a virtual image of a relatively large object (for example, fat or tumor mass) is likely to be generated. In this case, when the tomographic images having a virtual image are combined to generate a composite two-dimensional image, the virtual image also appears in the composite two-dimensional image.

In the technique disclosed in US2010/0135558A, each of the above-mentioned problems is not considered. Therefore, in a case in which the concentration of the subject image in the tomographic image is different from the concentration of the projection image, the concentration of the subject image in the composite two-dimensional image is also different from the concentration of the projection image. In addition, in a case in which a virtual image appears in the tomographic image, the virtual image appears in the composite two-dimensional image as in the tomographic image.

The invention has been made in view of the above-mentioned problems and an object of the invention is to provide an image processing device, a radiography system, an image processing method, and an image processing program that can generate tomographic images suitable for both radiographic interpretation and the generation of a composite two-dimensional image from projection images obtained by tomosynthesis imaging.

In order to achieve the object, according to a first aspect of the invention, there is provided an image processing device including: acquisition means for acquiring a plurality of projection images which are captured at different incident angles by irradiating a subject that is positioned between a radiation detector and a radiation emitting unit and of which a tomographic image is to be generated with radiation at different incident angles with respect to a direction normal to a tomographic plane of the tomographic image in a predetermined range while moving the radiation emitting unit; first tomographic image generation means for generating a first tomographic image which is emphasized according to a spatial frequency and is used for radiographic interpretation, on the basis of the projection images acquired by the acquisition means; second tomographic image generation means for generating a second tomographic image which is emphasized according to the spatial frequency and on which the degree of emphasis is different from the degree of emphasis on the first tomographic image, on the basis of the projection images; and two-dimensional image generation means for combining a plurality of the second tomographic images generated by the second tomographic image generation means to generate a composite two-dimensional image.

According to the invention, the acquisition means acquires the plurality of projection images which are captured by irradiating the subject that is positioned between the radiation detector and the radiation emitting unit and of which the tomographic image is to be generated with radiation at different incident angles with respect to the direction normal to the tomographic plane of the tomographic image in the predetermined range while moving the radiation emitting unit. In addition, in the invention, the first tomographic image generation means generates the first tomographic image which is emphasized according to the spatial frequency and is used for radiographic interpretation, on the basis of the projection images acquired by the acquisition means.

In the invention, the second tomographic image generation means generates the second tomographic image which is emphasized according to the spatial frequency and on which the degree of emphasis is different from the degree of emphasis on the first tomographic image, on the basis of the projection images. In the invention, the two-dimensional image generation means combines the plurality of second tomographic images generated by the second tomographic image generation means to generate a composite two-dimensional image.

That is, in the invention, the same projection image (group) is not used as each tomographic image, that is, the first tomographic image used for radiographic interpretation and the second tomographic image used to generate the composite two-dimensional image and projection images with different degrees of emphasis are separately generated. Therefore, in the invention, tomographic images which are suitable for both radiographic interpretation and the generation of a composite two-dimensional image are generated.

As such, according to the first aspect of the invention, the first tomographic image which is emphasized according to the spatial frequency and is used for radiographic interpretation is generated on the basis of the projection images and the second tomographic image which is emphasized according to the spatial frequency and on which the degree of emphasis is different from the degree of emphasis on the first tomographic image is generated on the basis of the projection images. Therefore, it is possible to generate tomographic images which are suitable for both radiographic interpretation and the generation of a composite two-dimensional image from the projection images obtained by tomosynthesis imaging.

However, for example, when the doctor interprets the tomographic image obtained by tomosynthesis imaging, an image in which a high frequency component in a spatial frequency domain is emphasized tends to be more preferable for use than the radiological image obtained by general two-dimensional imaging. The reason is as follows: in general, the doctor interprets tomographic images in a plurality of tomographic planes which are switched at a high speed and are displayed as a moving image, in order to prevent a relatively small object, such as a calcification, from being overlooked.

However, when a filtering process is performed with a high degree of emphasis on a high frequency component in the projection image during the reconstruction of the tomographic image used for radiographic interpretation from the projection image, a virtual image is likely to be generated in the tomographic image due to overemphasis. In this case, when the tomographic images are combined to generate a composite two-dimensional image, a virtual image is also generated in the generated composite two-dimensional image.

In the first aspect of the invention, the first tomographic image generation means may generate, as the first tomographic image, a tomographic image on which the degree of emphasis increases as the spatial frequency increases, on the basis of the projection images. The second tomographic image generation means may generate, as the second tomographic image, a tomographic image which is emphasized less than the first tomographic image and on which the degree of emphasis increases as the spatial frequency increases, on the basis of the projection images.

That is, in the invention, the first tomographic image which is used for radiographic interpretation and on which the degree of emphasis increases as the spatial frequency increases is generated. Therefore, in the invention, a tomographic image which is suitable for radiographic interpretation and suits a doctor's preference is generated. In addition, in the invention, the second tomographic image which is used to generate the composite two-dimensional image and is emphasized less than the first tomographic image and on which the degree of emphasis increases as the spatial frequency increases is generated, independently of the first tomographic image. Therefore, in the invention, a tomographic image which is suitable for generating a composite two-dimensional image and in which the generation of a virtual image due to overemphasis is suppressed is generated.

As such, according to the invention, the first tomographic image which is used for radiographic interpretation and on which the degree of emphasis increases as the spatial frequency increases is generated on the basis of the projection images and the second tomographic image which is used to generate the composite two-dimensional image and is emphasized less than the first tomographic image and on which the degree of emphasis increases as the spatial frequency increases is generated on the basis of the projection images. Therefore, it is possible to generate tomographic images which are suitable for both radiographic interpretation and the generation of a composite two-dimensional image from the projection images obtained by tomosynthesis imaging.

In particular, in the invention, the first tomographic image generation means may perform a process which increases the degree of emphasis on the projection image as the spatial frequency increases and may generate the first tomographic image, using reconstruction using the projection image subjected to the emphasis process. The second tomographic image generation means may perform a process which sets the degree of emphasis on the projection image to be less than the degree of emphasis on the first tomographic image and increases the degree of emphasis on the projection image as the spatial frequency increases and may generate the second tomographic image, using reconstruction using the projection image subjected to the emphasis process.

In the invention, the first tomographic image generation means may generate a tomographic image, using reconstruction using the projection image, and may perform a process which increases the degree of emphasis on the tomographic image as the spatial frequency increases to generate the first tomographic image. The second tomographic image generation means may generate a tomographic image, using reconstruction using the projection image, and may perform a process which sets the degree of emphasis on the tomographic image to be less than the degree of emphasis on the first tomographic image and increases the degree of emphasis on the tomographic image as the spatial frequency increases to generate the second tomographic image.

In the first aspect of the invention, the first tomographic image generation means and the second tomographic image generation means may determine a spatial frequency range in which the emphasis is performed, on the basis of the size of an object of interest during the radiographic interpretation.

The image processing device according to the first aspect of the invention may further include display means for displaying at least one of the first tomographic image generated by the first tomographic image generation means and the composite two-dimensional image generated by the two-dimensional image generation means.

The image processing device according to the first aspect of the invention may further include processing means for performing frequency processing which increases the degree of emphasis as the incident angle increases and attenuates a predetermined low frequency component of a spatial frequency of the projection image relative to a high frequency component having a higher spatial frequency than the low frequency component. The first tomographic image generation means may generate the first tomographic image on the basis of the projection image subjected to the frequency processing by the processing means. The second tomographic image generation means may generate the second tomographic image on the basis of the projection image subjected to the frequency processing by the processing means.

In particular, in the invention, the processing means may perform, as the frequency processing, at least one of a process which attenuates the low frequency component of the projection image and a process which emphasizes the high frequency component of the projection image.

The image processing device according to the first aspect of the invention may further include processing means for performing frequency processing which attenuates a predetermined low frequency component of a spatial frequency of a projection image in which the incident angle is equal to or greater than a predetermined first threshold value relative to a high frequency component having a higher spatial frequency than the low frequency component. The first tomographic image generation means may generate the first tomographic image on the basis of a projection image in which the incident angle is less than the predetermined first threshold value and the projection image subjected to the frequency processing by the processing means. The second tomographic image generation means may generate the second tomographic image on the basis of the projection image in which the incident angle is less than the predetermined first threshold value and the projection image subjected to the frequency processing by the processing means.

In particular, in the invention, the processing means may perform, as the frequency processing, at least one of a process which attenuates the low frequency component of the projection image in which the incident angle is equal to or greater than the predetermined first threshold value and a process which emphasizes the high frequency component of the projection image in which the incident angle is equal to or greater than the predetermined first threshold value.

In the first aspect of the invention, when performing the frequency processing, the processing means may increase the degree of relative attenuation of the low frequency component as the incident angle increases.

In the first aspect of the invention, at least one of the first tomographic image generation means and the second tomographic image generation means may generate the tomographic image on the basis of the projection image which is weighted according to the incident angle.

In the first aspect of the invention, the processing means may further perform frequency processing which emphasizes the low frequency component of a projection image, in which the incident angle is less than a second threshold value that is equal to or less than the first threshold value, relative to the high frequency component.

In the invention, when performing the frequency processing which relatively emphasizes the low frequency component, the processing means may increase the degree of relative emphasis on the low frequency component as the incident angle decreases.

In the first aspect of the invention, the two-dimensional image generation means may perform a projection process for a stacked image, which is obtained by stacking the plurality of second tomographic images generated by the second tomographic image generation means, in a predetermined direction or an addition process which adds values of corresponding pixels in the predetermined direction to generate the composite two-dimensional image.

In order to achieve the object, according to a second aspect of the invention, there is provided a radiography system including: a radiography apparatus that includes a radiation detector and a radiation emitting unit and irradiates a subject that is positioned between the radiation detector and the radiation emitting unit and of which a tomographic image is to be generated with radiation at different incident angles with respect to a direction normal to a tomographic plane of the tomographic image in a predetermined range while moving the radiation emitting unit to capture a plurality of projection images at different incident angles; and the image processing device that generates a first tomographic image which is used for radiographic interpretation, a second tomographic image which is used to generate a composite two-dimensional image, and the composite two-dimensional image from the plurality of projection images captured by the radiography apparatus.

In order to achieve the object, according to a third aspect of the invention, there is provided an image processing program that causes a computer to function as: acquisition means for acquiring a plurality of projection images which are captured at different incident angles by irradiating a subject that is positioned between a radiation detector and a radiation emitting unit and of which a tomographic image is to be generated with radiation at different incident angles with respect to a direction normal to a tomographic plane of the tomographic image in a predetermined range while moving the radiation emitting unit; first tomographic image generation means for generating a first tomographic image which is emphasized according to a spatial frequency and is used for radiographic interpretation, on the basis of the projection images acquired by the acquisition means; second tomographic image generation means for generating a second tomographic image which is emphasized according to the spatial frequency and on which the degree of emphasis is different from the degree of emphasis on the first tomographic image, on the basis of the projection images; and two-dimensional image generation means for combining a plurality of the second tomographic images generated by the second tomographic image generation means to generate a composite two-dimensional image.

In order to achieve the object, according to a fourth aspect of the invention, there is provided an image processing method including: an acquisition step of acquiring a plurality of projection images which are captured at different incident angles by irradiating a subject that is positioned between a radiation detector and a radiation emitting unit and of which a tomographic image is to be generated with radiation at different incident angles with respect to a direction normal to a tomographic plane of the tomographic image in a predetermined range while moving the radiation emitting unit; a first tomographic image generation step of generating a first tomographic image which is emphasized according to a spatial frequency and is used for radiographic interpretation, on the basis of the projection images acquired in the acquisition step; a second tomographic image generation step of generating a second tomographic image which is emphasized according to the spatial frequency and on which the degree of emphasis is different from the degree of emphasis on the first tomographic image, on the basis of the projection images; and a two-dimensional image generation step of combining a plurality of the second tomographic images generated in the second tomographic image generation step to generate a composite two-dimensional image.

The radiography system, the image processing program, and the image processing method have the same operation as that in the first aspect. Therefore, it is possible to generate tomographic images which are suitable for both radiographic interpretation and the generation of a composite two-dimensional image from projection images obtained by tomosynthesis imaging.

As described above, according to the invention, it is possible to generate tomographic images which are suitable for both radiographic interpretation and the generation of a composite two-dimensional image from projection images obtained by tomosynthesis imaging.

BRIEF DESCRIPTION OF THE DRAWINGS

FIG. 6C is a diagram illustrating tomographic images corresponding to slice positions S1 and S2 in FIG. 6B.

FIG. 8A is a perspective view schematically illustrating the position of each image to be illustrated in FIGS. 8B1 to 8B3.

FIGS. 8B1 to 8B3 are diagrams illustrating a combination of a tomographic image corresponding to the position S1 of FIG. 8A which is parallel to a tomographic plane at a position where an object of interest is present in a depth direction and an image corresponding to a position S2 of FIG. 8A in the depth direction for each type of frequency processing in a case in which the reconstructed tomographic images are stacked in the depth direction so as to correspond to each slice position.

DESCRIPTION OF THE PREFERRED EMBODIMENTS

Hereinafter, embodiments of the invention will be described in detail with reference to the drawings. The embodiments do not limit the invention.

First Embodiment

Figure 1:
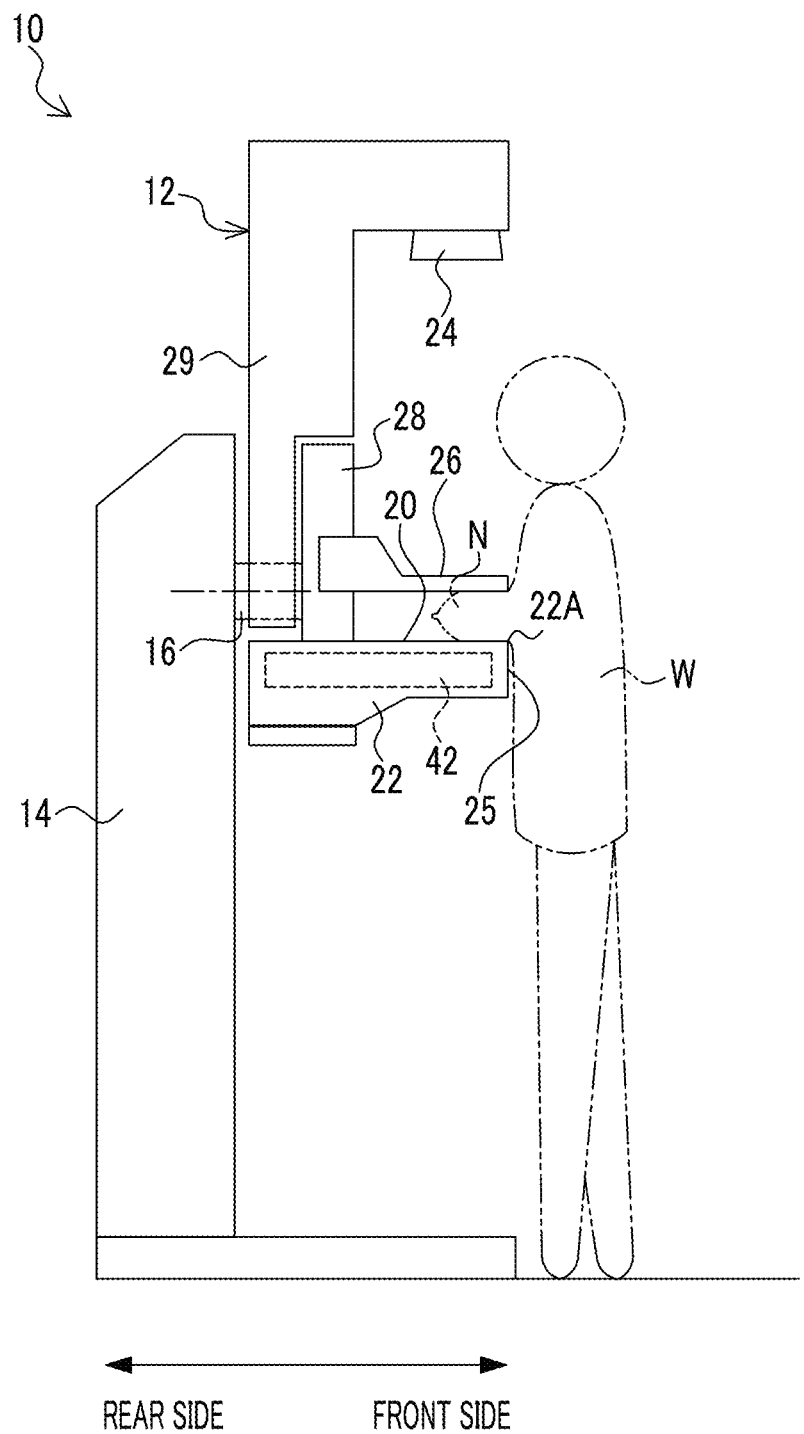
FIG. 1 is a side view illustrating an example of the structure of a radiography apparatus according to an embodiment.
Figure 2:
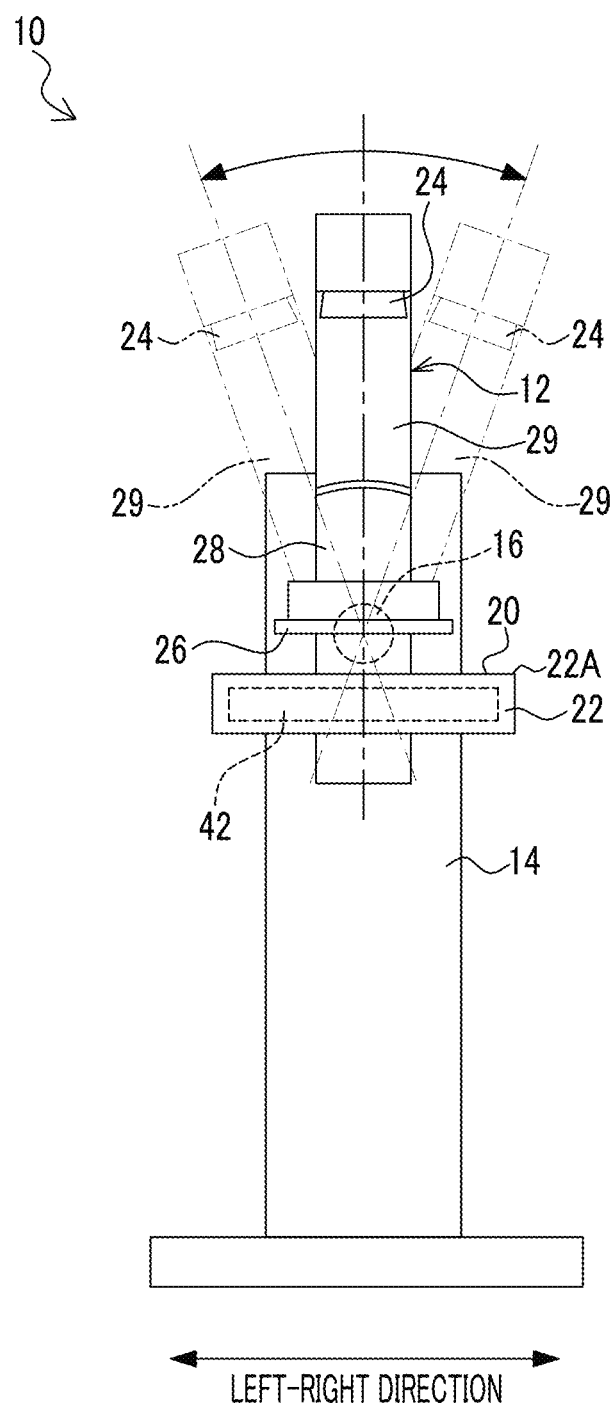
FIG. 2 is front view illustrating an example of the structure of the radiography apparatus according to the embodiment during imaging.
Figure 3:
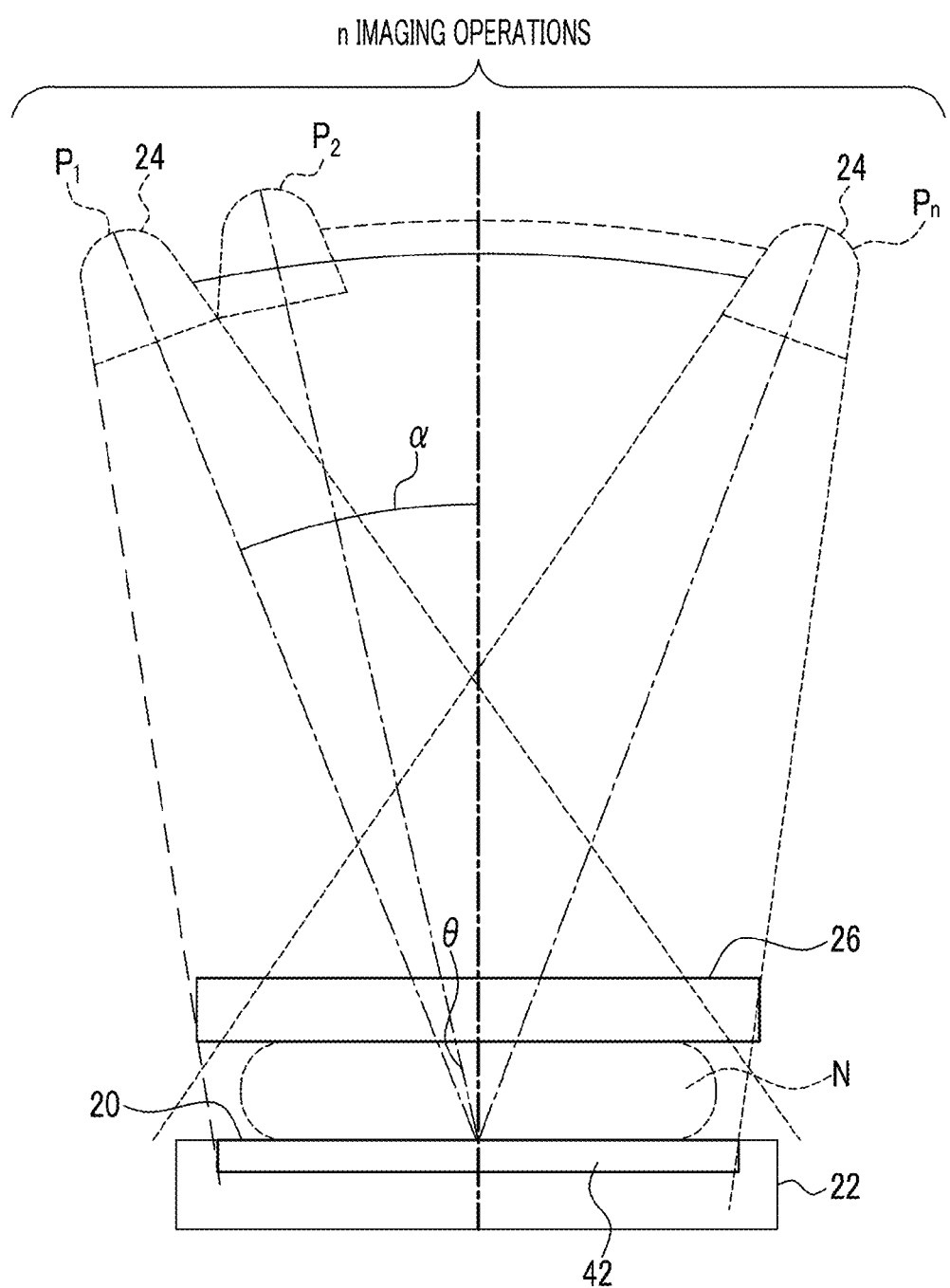
FIG. 3 is a front view schematically illustrating the radiography apparatus according to the embodiment during imaging.

As illustrated in FIGS. 1 to 3, a radiography apparatus 10 according to this embodiment captures an image of the breast N of a subject W that stands up, using radiation (for example, X-rays), and is also referred to as, for example, a mammography apparatus. In the following description, a front side which is close to the subject W in a case in which the subject W faces the radiography apparatus 10 during imaging is referred to as the front side of the radiography apparatus 10, a back side which is away from the subject W in a case in which the subject W faces the radiography apparatus 10 is referred to as the rear side of the radiography apparatus 10, and the left-right direction of the subject W in a case in which the subject W faces the radiography apparatus 10 is referred to as the left-right side of the radiography apparatus 10 (see each arrow illustrated in FIGS. 1 and 2).

The imaging target of the radiography apparatus 10 is not limited to the breast N and may be, for example, another part of the body or an object. The radiography apparatus 10 may be an apparatus which captures an image of the breast N of the subject W that sits on a chair (including a car seat) or an apparatus which can individually capture images of the left and right breasts N of the subject W in a state in which at least the upper part of the body of the subject W stands up.

As illustrated in FIG. 1, the radiography apparatus 10 includes a measurement unit 12 which is provided on the front side of the apparatus and has a substantially C shape in a side view and a base portion 14 which supports the measurement unit 12 from the rear side of the apparatus.

The measurement unit 12 includes a radiographic stand 22 including a planar imaging plane 20 which comes into contact with the breast N of the subject W that is in a standing state, a compression plate 26 for compressing the breast N against the imaging plane 20 of the radiographic stand 22, and a holding portion 28 which supports the radiographic stand 22 and the compression plate 26. The compression plate 26 is made of a member which transmits radiation.

In addition, the measurement unit 12 is provided with a radiation source 30 (see FIG. 4), such as a radiation tube, and includes a radiation emitting unit 24 that emits radiation for examination from the radiation source 30 to the imaging plane 20 and a support portion 29 that is separated from the holding portion 28 and supports the radiation emitting unit 24.

Furthermore, the measurement unit 12 is provided with a rotating shaft 16 that is rotatably supported by the base portion 14. The rotating shaft 16 is fixed to the support portion 29. The rotating shaft 16 is rotated integrally with the support portion 29.

The holding portion 28 can switch between a state in which the holding portion 28 is connected to the rotating shaft 16 and is rotated integrally with the rotating shaft 16 and a state in which the holding portion 28 is separated from the rotating shaft 16 and the rotating shaft 16 rotates idle. Specifically, gears are provided in the rotating shaft 16 and the holding portion 28 and switch between an engaged state and a disengaged state.

Various types of mechanical elements can be used to switch between the transmission and non-transmission of the torque of the rotating shaft 16.

The holding portion 28 supports the radiographic stand 22 and the radiation emitting unit 24 such that the imaging plane 20 and the radiation emitting unit 24 are spaced at a predetermined distance, and supports the compression plate 26 such that the compression plate 26 can slide and the gap between the compression plate 26 and the imaging plane 20 is variable.

The imaging plane 20 with which the breast N comes into contact is made of carbon in terms of the transmittance or intensity of radiation. A radiation detector 42 that is irradiated with radiation which has passed through the breast N and the imaging plane 20 and detects the radiation is provided in the radiographic stand 22. The radiation detected by the radiation detector 42 is visualized and a radiological image is generated.

The radiography apparatus 10 according to this embodiment can irradiate the breast N at different incident angles (while changing the incident angle) in a predetermined range and can capture the images of the breast N at different incident angles (tomosynthesis imaging).

FIGS. 2 and 3 illustrate the posture of the radiography apparatus 10 during tomosynthesis imaging. As illustrated in FIGS. 2 and 3, the support portion 29 which supports the radiation emitting unit 24 and supports the radiographic stand 22 through the holding portion 28 is inclined and then the tomosynthesis imaging is performed.

In the radiography apparatus 10 according to this embodiment, as illustrated in FIG. 3, in a case in which the breast N is irradiated with radiation at different incident angles in a predetermined range (for example, in a range of ±20°) to capture the image of the breast N, the rotating shaft 16 rotates idle with respect to the holding portion 28 such that the radiographic stand 22 and the compression plate 26 do not move and the support portion 29 is rotated such that only the radiation emitting unit 24 is moved in an arc shape. In this embodiment, as illustrated in FIG. 3, the position of the radiation emitting unit 24 is moved from an angle α at a predetermined angular interval of θ and imaging is performed at n positions, that is, positions P1 to Pn of the radiation emitting unit 24.

In general, in a case in which tomosynthesis imaging is performed, the breast N of the subject W is irradiated with radiation n times. Therefore, a dose of radiation is reduced such that an exposure dose does not increase. For example, radiation is emitted such that the total dose of radiation during n irradiation operations is equal to that during general two-dimensional imaging (general imaging in which the subject is irradiated with radiation at a fixed position without moving the radiation source 30 and then an image of the subject is captured).

The radiography apparatus 10 according to this embodiment can perform both craniocaudal (CC) imaging and mediolateral-oblique (MLO) imaging for the breast N. During the CC imaging, the posture of the holding portion 28 is adjusted, with the imaging plane 20 up, and the posture of the support portion 29 is adjusted, with the radiation emitting unit 24 located above the imaging plane 20. Then, the radiation emitting unit 24 emits radiation to the breast N in a direction from the head to the feet of the subject W that is in a standing state and the CC imaging is performed. During the MLO imaging, in general, the posture of the holding portion 28 is adjusted, with the radiographic stand 22 rotated at an angle that is equal to or greater than 45° and less than 90°, as compared to the CC imaging, and is positioned such that the armpit of the subject W comes into contact with a side wall corner portion 22A of the radiographic stand 22 which is on the front side of the apparatus. Then, the radiation emitting unit 24 emits radiation to the breast N in a direction from the center of the body axis of the subject W to the outside and the MLO imaging is performed.

A chest wall surface 25 with which a chest part below the breast N of the subject W comes into contact during imaging is formed on the surface of the radiographic stand 22 that is disposed on the front side of the apparatus. In this embodiment, the chest wall surface 25 has a planar shape.

Figure 4:
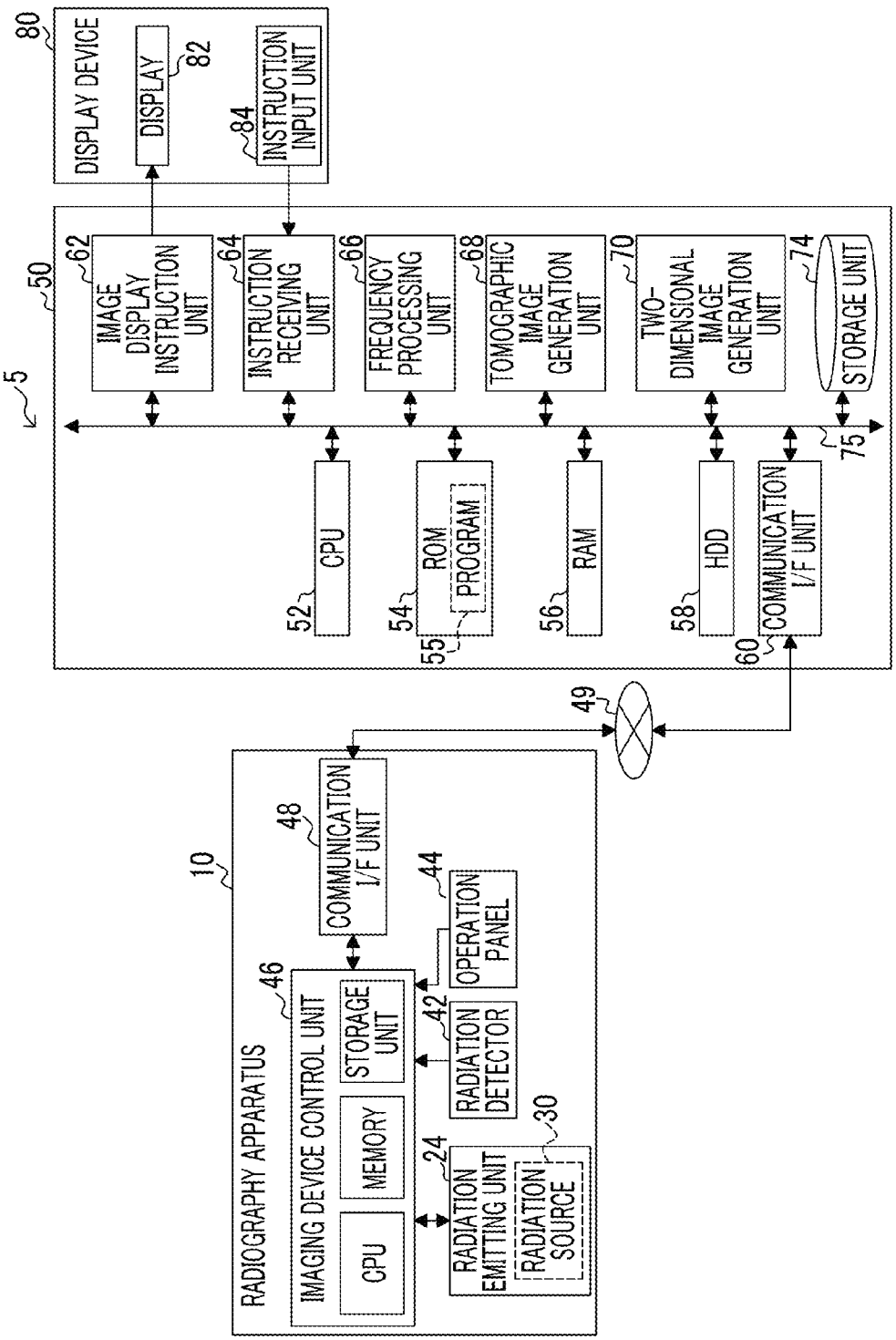
FIG. 4 is a block diagram illustrating an example of the structure of a radiography system according to the embodiment.

FIG. 4 illustrates an example of the structure of a radiography system 5 according to this embodiment.

As illustrated in FIG. 4, the radiography system 5 according to this embodiment includes the radiography apparatus 10, an image processing device 50, and a display device 80.

The radiography apparatus 10 includes the radiation emitting unit 24 and the radiation detector 42, as described above, and also includes an operation panel 44, an imaging device control unit 46, and a communication I/F unit 48.

The imaging device control unit 46 according to this embodiment has a function of controlling the overall operation of the radiography apparatus 10 and includes a central processing unit (CPU), a memory including a read only memory (ROM) and a random access memory (RAM), and a non-volatile storage unit such as a hard disk drive (HDD) or a flash memory. The imaging device control unit 46 is connected to the radiation emitting unit 24, the radiation detector 42, the operation panel 44, and the communication I/F unit 48.

When an irradiation instruction is received from the operator through the operation panel 44 (for example, an exposure switch), the imaging device control unit 46 directs the radiation source 30 provided in the radiation emitting unit 24 to emit radiation to the imaging plane 20 according to an imaging menu (which will be described in detail below) which is set on the basis of the designated exposure conditions. In this embodiment, the radiation source 30 emits cone beam radiation (for example, a cone-shaped X-ray beam).

The radiation detector 42 receives radiation which carries image information, records the image information, and outputs the recorded image information. The radiation detector 42 is, for example, a flat panel detector (FPD) that includes a radiation sensitive layer and converts radiation into digital data. The radiation sensitive layer can be provided substantially in parallel to the imaging plane 20. When radiation is emitted, the radiation detector 42 outputs image information indicating a radiological image to the imaging device control unit 46. In this embodiment, the radiation detector 42 receives the radiation which has passed through the breast N and image information indicating a radiological image is obtained.

The operation panel 44 is used to set, for example, various kinds of operation information including imaging conditions and various kinds of operation instructions.

The imaging conditions set by the operation panel 44 include exposure conditions including a tube voltage, a tube current, and an irradiation time and information such as posture information. In addition, the posture information designated by the operation panel 44 includes information indicating imaging positions (including incident angles) in a case in which radiation is incident on the breast N at a plurality of incident angles.

In addition, for example, the exposure conditions, various kinds of operation information including the posture information, and various kinds of operation instructions may be set by the operator through the operation panel 44, may be obtained from other control devices (radiology information system (RIS) (system that manages information about, for example, medical examination and diagnosis using radiation)), or may be stored in the storage unit in advance.

When various kinds of information are set through the operation panel 44, the imaging device control unit 46 directs the radiation emitting unit 24 to emit radiation to the part (breast N), of which the image is to be captured, in the subject W according to the imaging menu which is set on the basis of various kinds of set information, thereby capturing a radiological image. In a case in which tomosynthesis imaging is performed for the breast N, the imaging device control unit 46 adjusts the posture of the holding portion 28, with the imaging plane 20 up, and adjusts the posture of the support portion 29, with the radiation emitting unit 24 located above the imaging plane 20. Then, as illustrated in FIG. 3, the imaging device control unit 46 rotates the support portion 29 on the basis of the imaging conditions such that the radiation emitting unit 24 is moved from the angle α at an angular interval of θ in an arch shape and directs the radiation source 30 provided in the radiation emitting unit 24 to emit radiation. In this way, n radiological images in which the incident angles of radiation are different from each other are obtained.

The communication I/F unit 48 is a communication interface which has a function of receiving and transmitting, for example, a captured radiological image or various kinds of information between the radiography apparatus 10 and the image processing device 50 through a network 49.

The image processing device 50 according to this embodiment has a function of generating a tomographic image which is reconstructed from the radiological image acquired from the radiography apparatus 10 and has a function of performing image processing for enabling, for example, a doctor to observe an object of interest, such as a tumor mass or a calcification, for the radiological image. Hereinafter, for example, the doctor who observes the captured radiological image or the generated tomographic image or diagnoses a tumor is referred to as a "user" and the radiological image which is obtained by the detection of radiation by the radiation detector 42 during tomosynthesis imaging in the radiography apparatus 10 is referred to as a "projection image".

The image processing device 50 includes a CPU 52, a ROM 54, a RAM 56, an HDD 58, a communication I/F unit 60, an image display instruction unit 62, an instruction receiving unit 64, a frequency processing unit 66, a tomographic image generation unit 68, a two-dimensional image generation unit 70, and a storage unit 74. These units are connected to each other so as to transmit and receive information through a bus 75 such as a control bus or a data bus.

The CPU 52 controls, for example, the overall operation of the image processing device 50. Specifically, the CPU 52 executes a program 55 (including a first image generation processing program which will be described below) stored in the ROM 54 to perform control. In this embodiment, the program 55 is stored in the ROM 54 in advance. However, the invention is not limited thereto. For example, the program 55 may be stored in a recording medium, such as a CD-ROM or a removable disk and may be installed from the recording medium to the ROM 54, or may be installed from an external device to the ROM 54 through a communication line such as the Internet. In addition, the RAM 56 ensures a work area when the CPU 52 executes the program 55. The HDD 58 stores and retains various kinds of data.

The communication I/F unit 60 is a communication interface which has a function of transmitting and receiving, for example, a captured radiological image or various kinds of information between the image processing device 50 and the radiography apparatus 10 through the network 49.

The image display instruction unit 62 has a function of instructing a display 82, which will be described below, in the display device 80 to display a radiological image.

The display device 80 according to this embodiment has a function of displaying the captured radiological image and includes the display 82 on which the radiological image is displayed and an instruction input unit 84. The instruction input unit 84 may be, for example, a touch panel display, a keyboard, or a mouse. The user can input an instruction related to the display of a radiological image, using the instruction input unit 84. The instruction receiving unit 64 has a function of receiving the instruction which is input from the user through the instruction input unit 84 of the display device 80.

The frequency processing unit 66 according to this embodiment performs frequency processing for the projection image such that a frequency component in a predetermined spatial frequency range is emphasized and attenuated according to an emphasis coefficient indicating the degree of emphasis.

In this embodiment, the frequency processing unit 66 increases the degree of emphasis on the frequency component as the emphasis coefficient increases over a predetermined threshold value (1.0 in this embodiment) and increases the degree of attenuation of the frequency component as the emphasis coefficient decreases below the threshold value.

For example, the technique disclosed in JP1998-63838A (JP-H10-63838A) is applied as the frequency processing. Specifically, first, the frequency processing unit 66 performs a process, which changes the degree of reduction in the sharpness of an image to reduce the sharpness, for the projection image to generate a plurality of images (hereinafter, referred to as "unsharp images") which have a lower sharpness than the projection image and have different sharpnesses. In this embodiment, a filtering process using a Gaussian filter is applied as the process of reducing the sharpness. However, the invention is not limited thereto. For example, other known methods, such as a filtering process using a moving average filter, may be used.

Then, the frequency processing unit 66 performs a conversion process using a predetermined conversion function for each difference between the images with sharpnesses that are closest to each other, on the basis of the projection image and each unsharp image, and adds the converted differences to generate an image. Then, the frequency processing unit 66 adds the projection image and an image, which is obtained by emphasizing and attenuating the image obtained by the addition according to a predetermined emphasis coefficient and generates the added image as an image subjected to the frequency processing.

As described above, in this embodiment, the frequency processing unit 66 emphasizes and attenuates frequency components in a predetermined spatial frequency range of the projection image according to the emphasis coefficient to generate an image. Here, the spatial frequency range and the emphasis coefficient which are applied when the frequency processing unit 66 performs frequency processing for the projection image may be stored in storage means, such as the ROM 54, in advance, may be input by the user through the instruction input unit 84, or may be input from an external device through the communication I/F unit 60. Since the above-mentioned frequency processing is a known technique in the related art, the detailed description thereof will not be repeated.

The tomographic image generation unit 68 has a function of reconstructing the projection images which have been subjected to the frequency processing by the frequency processing unit 66 to generate tomographic images that are parallel to the imaging plane 20 at a predetermined slice interval. Here, the term "parallel" means "being parallel" in the allowable range of an error caused by, for example, a change in the radiography apparatus 10 over time or a change in environmental conditions.

In this embodiment, the tomographic image generation unit 68 generates tomographic images from a plurality of projection images, which have been captured with the radiation emitting unit 24 (radiation source 30) moved to P1, P2, P3, . . . , Pn and then subjected to the frequency processing by the frequency processing unit 66, at a predetermined slice interval. The projection position of the object of interest on the radiological image varies depending on the incident angle of radiation. Therefore, in this embodiment, the tomographic image generation unit 68 acquires the imaging conditions when the radiological image is captured by the radiography apparatus 10. Then, the tomographic image generation unit 68 calculates the amount of movement of the object of interest in the plurality of radiological images on the basis of the incident angle of radiation included in the acquired imaging conditions and reconstructs the tomographic images on the basis of a known reconstruction method such as a back projection method or a shift-and-add method.

In addition to the back projection method or the shift-and-add method, a known CT reconstruction method (for example, the above-mentioned FBP method) can be used as the reconstruction method. The FBP method is a reconstruction method which considers parallel plane tomographic scanning in tomographic imaging as a part of cone beam CT scanning and is an expanded version of the filter back projection method. In addition, the iterative reconstruction method disclosed in JP2011-125698A can be used as the reconstruction method. The iterative reconstruction method is a reconstruction method for CT and can be applied to reconstruction during tomosynthesis imaging, similarly to the FBP method.

The two-dimensional image generation unit 70 according to this embodiment performs a projection process for a stacked image (three-dimensional image), which is obtained by stacking a plurality of tomographic images generated by the tomographic image generation unit 68, along a predetermined direction to generate a composite two-dimensional image. In this embodiment, the two-dimensional image generation unit 70 performs the projection process to generate a composite two-dimensional image. However, the invention is not limited thereto. For example, the two-dimensional image generation unit 70 may perform an addition process which adds corresponding pixel values along a predetermined direction to generate a composite two-dimensional image.

Each of the frequency processing unit 66, the tomographic image generation unit 68, and the two-dimensional image generation unit 70 can be implemented by hardware which is formed by, for example, a general electronic circuit, an application specific integrated circuit (ASIC), or a field programmable gate array (FPGA).

The storage unit 74 according to this embodiment has a function of storing, for example, image information indicating each of the projection image captured by the radiography apparatus 10, the tomographic image generated by the tomographic image generation unit 68, and the composite two-dimensional image generated by the two-dimensional image generation unit 70 and is a large-capacity storage device such as a hard disk. In this embodiment, the storage unit 74 also stores the imaging conditions (for example, the incident angle of radiation) when the radiography apparatus 10 captures a radiological image.

Next, the operation of the radiography system 5 according to this embodiment will be described with reference to the drawings.

In a case in which a radiological image is captured, when an imaging menu is set, the radiography apparatus 10 captures the radiological image according to the imaging menu.

In a case in which an imaging instruction to perform tomosynthesis imaging is input, as illustrated in FIG. 2, the radiography apparatus 10 adjusts the posture of the holding portion 28, with the imaging plane 20 up, and adjusts the posture of the support portion 29, the radiation emitting unit 24 positioned above the imaging plane 20.

The breast N of the subject W comes into contact with the imaging plane 20 of the radiography apparatus 10. In this state, when the operator operates the operation panel 44 to input a pressure start instruction, the radiography apparatus 10 moves the compression plate 26 to the imaging plane 20.

In this embodiment, in a case in which an instruction to perform tomosynthesis imaging is input to the operation panel 44 in this state, as illustrated in FIG. 3, the radiography apparatus 10 rotates only the support portion 29 to move the radiation emitting unit 24 in an arc shape from the angle α at a predetermined angular interval θ and emits radiation based on each imaging condition at each of the positions P1 to Pn of the radiation emitting unit 24. Each of the radiations which are individually emitted from the radiation emitting unit 24 passes through the breast N and reaches the radiation detector 42.

When radiation is emitted, the radiation detector 42 outputs image information indicating each projection image formed by the emitted radiation to the imaging device control unit 46. As described above, in a case in which the radiation emitting unit 24 emits radiation at the n positions P1 to Pn, image information about n projection images is output to the imaging device control unit 46.

The imaging device control unit 46 outputs each of the input image information items to the image processing device 50. As described above, in a case in which the radiation emitting unit 24 emits radiation at the n positions P1 to Pn, the CPU of the imaging device control unit 46 outputs image information about n projection images to the image processing device 50.

The image processing device 50 according to this embodiment performs frequency processing for the projection image, reconstructs a tomographic image (hereinafter, referred to as a "first tomographic image") used for radiographic interpretation, and displays the first tomographic image on the display device 80 through the image display instruction unit 62. In addition, the image processing device 50 performs frequency processing for the projection image and reconstructs a tomographic image (hereinafter, referred to as a "second tomographic image") used to generate a composite two-dimensional image. Then, the image processing device 50 generates a composite two-dimensional image from the second tomographic image and displays the composite two-dimensional image on the display device 80 through the image display instruction unit 62.

In the image processing device 50 according to this embodiment, the frequency processing unit 66 and the tomographic image generation unit 68 generate, as the first tomographic image, a tomographic image on which the degree of emphasis increases as the spatial frequency increases, on the basis of the projection image. In addition, in the image processing device 50 according to this embodiment, the frequency processing unit 66 and the tomographic image generation unit 68 generate, as the second tomographic image, a tomographic image on which the degree of emphasis is less than the degree of emphasis on the first tomographic image and increases as the spatial frequency increases, on the basis of the projection image.

Figure 5:
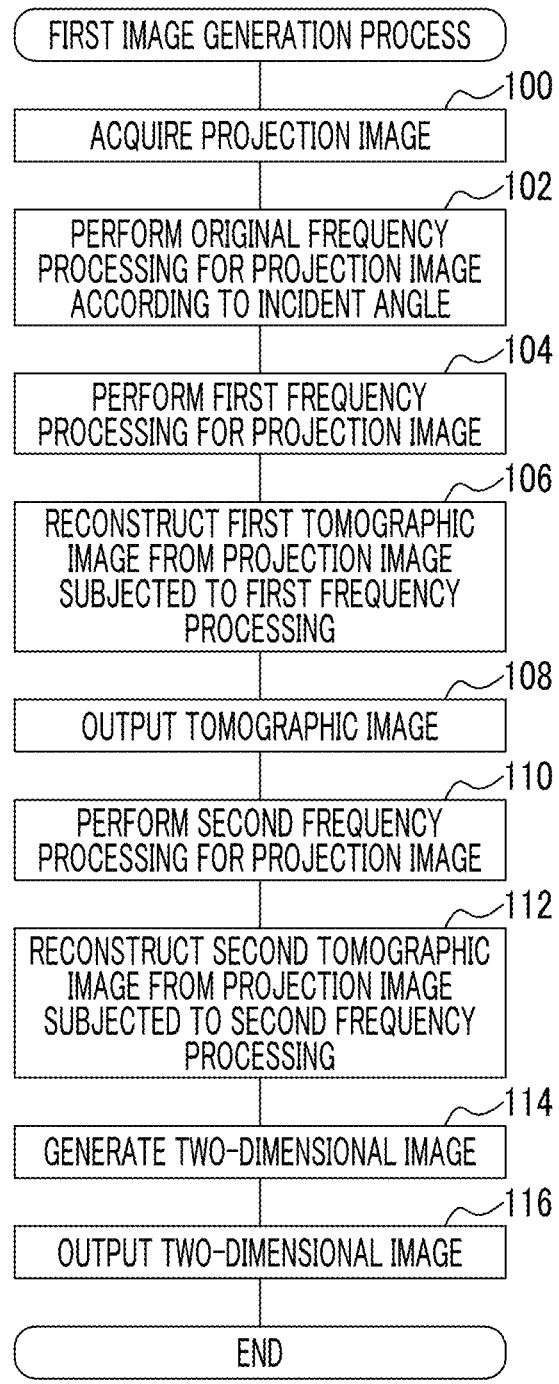
FIG. 5 is a flowchart illustrating the flow of the process of a first image generation processing program according to a first embodiment.

FIG. 5 is a flowchart illustrating the flow of the process of a first image generation processing program which is executed by the CPU 52 of the image processing device 50 according to this embodiment.

In Step 100 of FIG. 5, the CPU 52 acquires image information about a plurality of (here, n) projection images from the radiography apparatus 10.

In Step 102, the CPU 52 controls the frequency processing unit 66 such that frequency processing (hereinafter, referred to as "original frequency processing") is performed for the projection images according to the incident angle. In this embodiment, the frequency processing unit 66 performs frequency processing which attenuates a low frequency component relative to a high frequency component in the projection image in which the incident angle during imaging is equal to or greater than a predetermined first threshold value. Here, an example of the frequency processing which attenuates the low frequency component relative to the high frequency component is as follows: an emphasis coefficient for a high frequency component is 1.0; an emphasis coefficient for a low frequency component is less than 1.0; a process of emphasizing the high frequency component is not performed; and a process of attenuating the low frequency component (hereinafter, referred to as a "low frequency component attenuation process") is performed.

In this embodiment, the spatial frequency range including an object that is larger than the object of interest to be observed by the user is regarded as a low frequency range and the object included in the low frequency domain is regarded as the low frequency component. In this embodiment, a spatial frequency range that is higher than the upper limit of the low frequency domain is regarded as a high frequency domain and an object included in the high frequency domain is regarded as the high frequency component. In this embodiment, the normal size (for example, 300 µm) of a calcification is applied as the size of the object of interest. However, the invention is not limited thereto. For example, the size of another object of interest, such as a tumor mass, may be applied.

Here, the process performed by the frequency processing unit 66 in Step 102 will be described in detail.

Figure 6A:
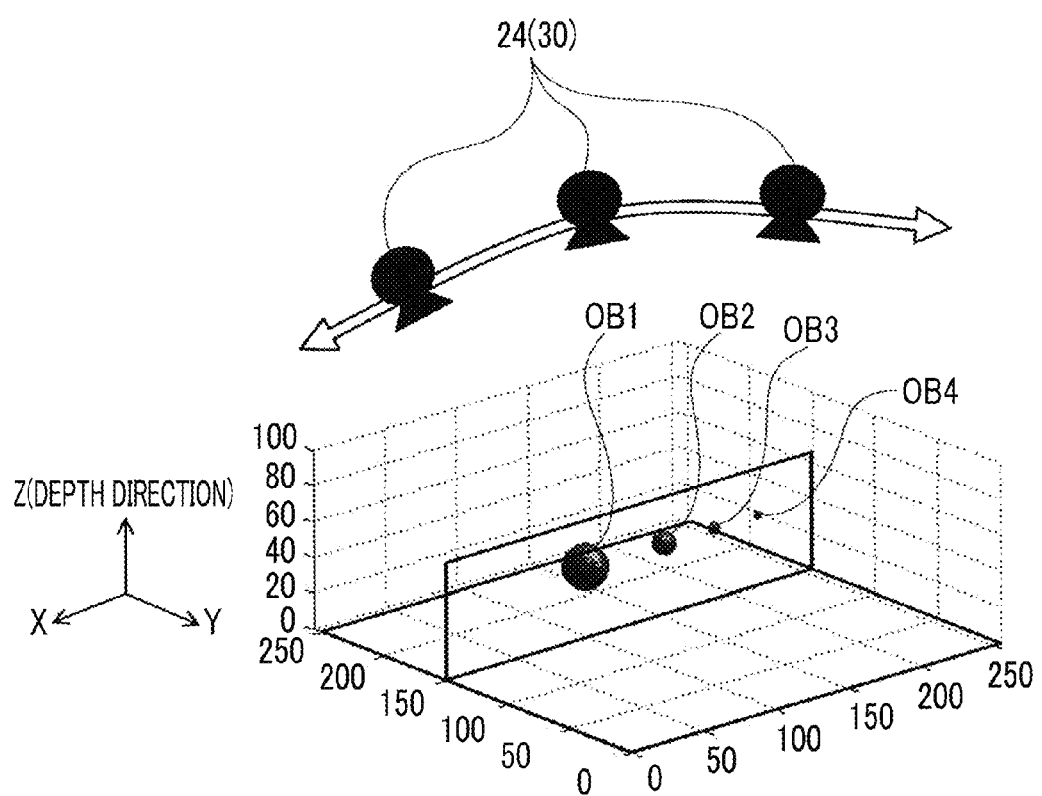
FIG. 6A is a diagram schematically illustrating an example of tomosynthesis imaging according to the embodiment.

FIG. 6A is a diagram schematically illustrating an example of the tomosynthesis imaging. The Z-axis indicates a coordinate value (distance from the detection surface) in a direction perpendicular to the detection surface of the radiation detector 42. In the detection surface of the radiation detector 42, Z is 0. Here, as illustrated in FIG. 6A, a case in which the radiation emitting unit 24 is moved and emits radiation to four objects OB1 to OB4 at three positions will be described. Among the four objects, the object OB1 is the largest and the object OB4 is the smallest.

Figure 6B:
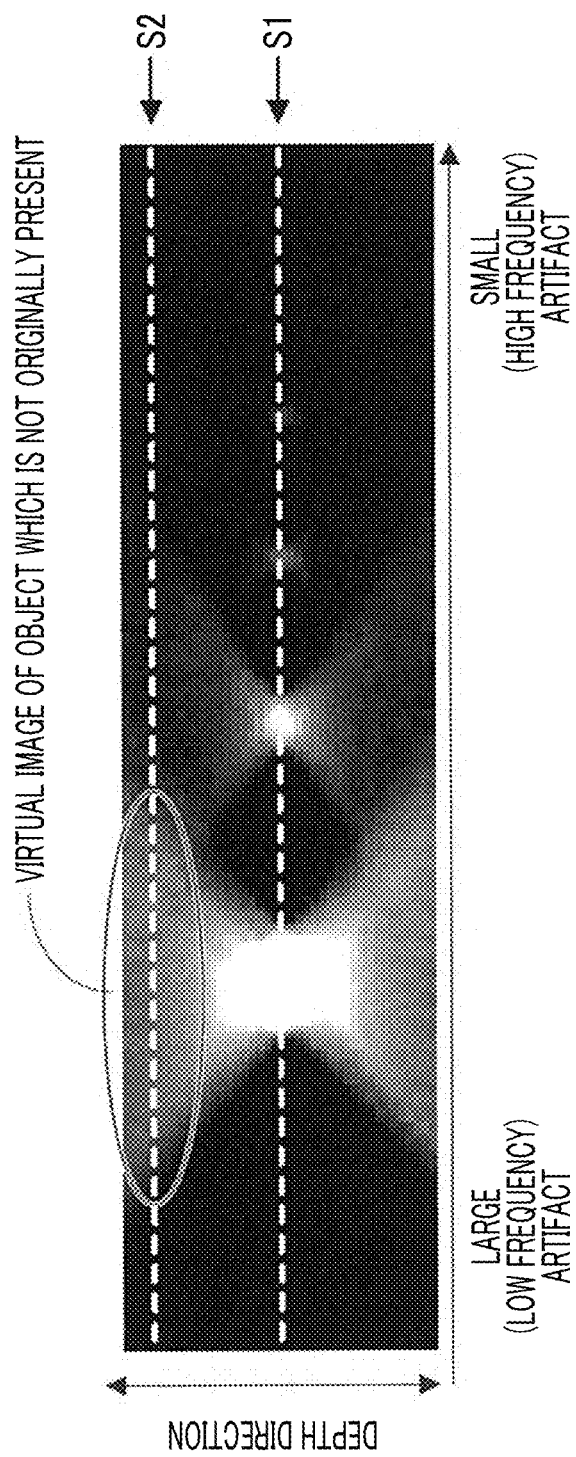
FIG. 6B is a cross-sectional view that is parallel to an X-Z plane at a position 150 in a Y-axis direction of FIG. 6A when frequency processing is not performed for any captured projection image and tomographic images are reconstructed and are stacked in a Z-axis direction (depth direction) so as to correspond to the slice position of each tomographic image.

FIG. 6B is a cross-sectional view that is parallel to the X-Z plane at a Y-axis position 150 when the original frequency processing is not performed for any captured projection image and the tomographic images are reconstructed and stacked in a depth direction (Z-axis direction) so as to correspond to the slice position of each tomographic image (see FIG. 6A). FIG. 6C illustrates the tomographic images corresponding to slice positions S1 and S2 in FIG. 6B.

As illustrated in FIG. 6B, the slice position S1 corresponds to a position where the object OB1 is actually present and the image of the object OB1 is clearly seen in the tomographic image at the slice position S1. However, although the object OB1 is not originally present at the slice position S2, the artifact of the object OB1 appears in the tomographic image at the slice position S2. As can be seen from FIGS. 6B and 6C, as the size of the object increases, the size of the artifact generated in the depth direction increases. When an image is converted into a spatial frequency domain, the image of an object with a large size is converted into a low frequency component and the image of an object with a small (fine) size is converted into a high frequency component. As such, in a case in which an image is represented by the spatial frequency domain, as the object has a lower frequency component, the size of the artifact in the depth direction increases. In addition, as the object has a higher frequency component, the size of the artifact in the depth direction decreases.

Figure 7:
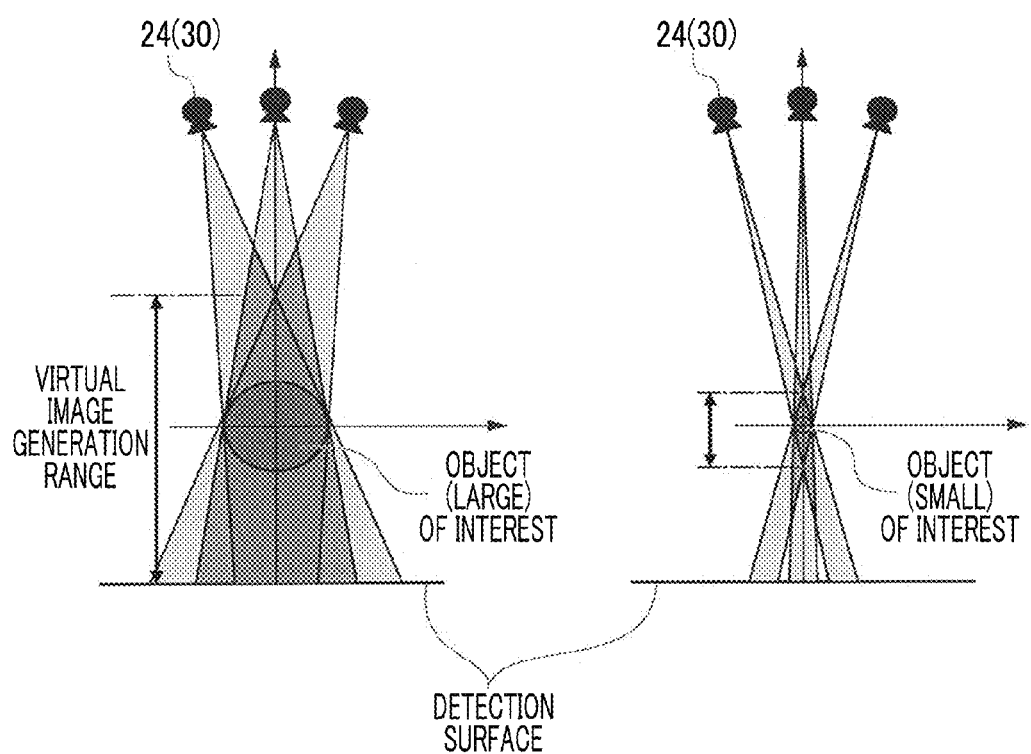
FIG. 7 is a front view schematically illustrating the reason why an artifact is generated.

As illustrated in FIG. 7, as the size of the object increases, the area irradiated with radiation increases. The radiation which has passed through the object is detected by the detection surface and the size of the object in the projection image increases. As the incident angle increases, the extension of the object to a region that is away from the region in which the object is actually present increases. When the tomographic images which are reconstructed from the projection images are stacked, the artifact of the object which extends in the depth direction is generated in the range in which the irradiation regions of radiation overlap each other in the depth direction. Therefore, as the size of the object increases, the size of the artifact in the depth direction increases.

For example, the FBP method using the first filter or the method for reconstructing the tomographic image using the second filter collectively performs a filtering process for a plurality of projection images and reconstructs the images to suppress an artifact. A case in which these methods are applied to collectively perform the filtering process for the projection images obtained by tomosynthesis imaging will be described.

FIGS. 8B1 to 8B3 illustrate a combination of a tomographic image which corresponds to the slice position S1 parallel to the detection surface of the radiation detector 42 at the position where the object of interest is present in the depth direction and an image which corresponds to a position S2 along the depth direction (see FIG. 8A). Here, combinations 8B1 to 8B3 of three patterns are illustrated. FIG. 8B1 illustrates a combination of ideal images which will be originally projected. FIG. 8B2 illustrates a combination of the images obtained by collectively performing the filtering process for all of the projection images using a low-pass filter (LPF) and reconstructing the processed images. FIG. 8B3 illustrates a combination of the images obtained by collectively performing the filtering process for all of the projection images using a high-pass filter (HPF) and reconstructing the processed images.

As illustrated in FIG. 8B2, when a low frequency components is collectively extracted and a high frequency component is attenuated, an artifact is generated in the depth direction. As described above, as the size of the object increases, the size of the artifact increases.

As illustrated in FIG. 8B3, when a high frequency components is collectively extracted and a low frequency component is attenuated, the size of the artifact decreases (the artifact is inconspicuous). For a large object, only the contour of the object remains and information about a low frequency component in the object, that is, concentration information is lost. The reason is that only a portion in which a change in concentration is large is extracted by the HPF and a region having a low frequency component in which a change in concentration is small is not extracted and is lost.

In a case in which the radiological image of the breast is interpreted by mammography, for example, fat, the mammary gland, and lesion (tumor mass) (object of interest) to be interpreted are classified into low frequency components with a relatively large size. Therefore, in the original frequency processing according to this embodiment, frequency processing is not collectively performed for all of the projection images and frequency processing which attenuates a low frequency component relative to a high frequency component in the projection image in which the incident angle is equal to or greater than the first threshold value is performed. Therefore, a significant reduction in the image concentration of the object of interest is suppressed and the artifact of the tomographic image in which the object of interest is not originally present is inconspicuous.

Figure 9A:
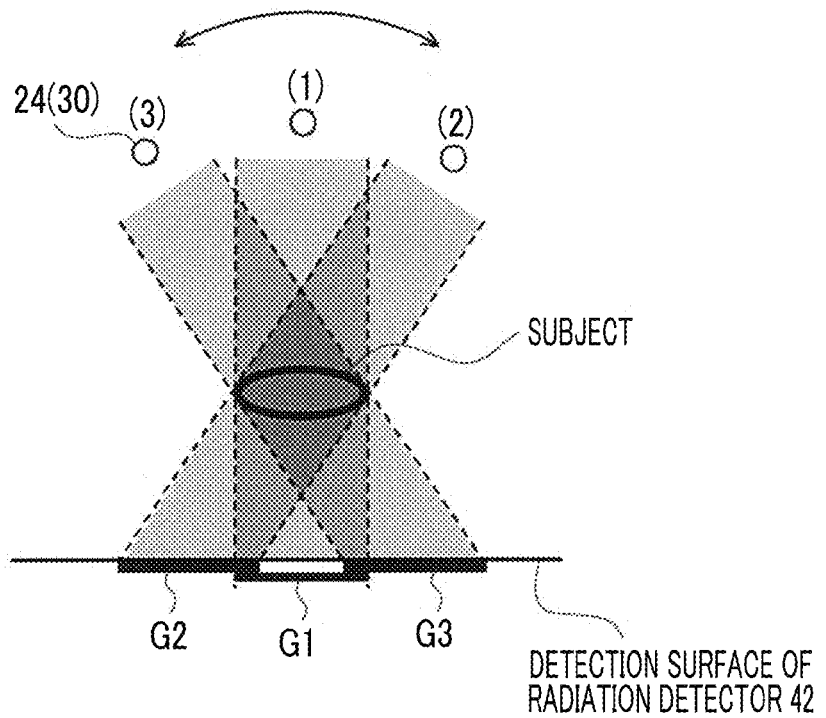
FIG. 9A is a front view schematically illustrating a case in which frequency processing according to the embodiment is not performed.
Figure 9B:
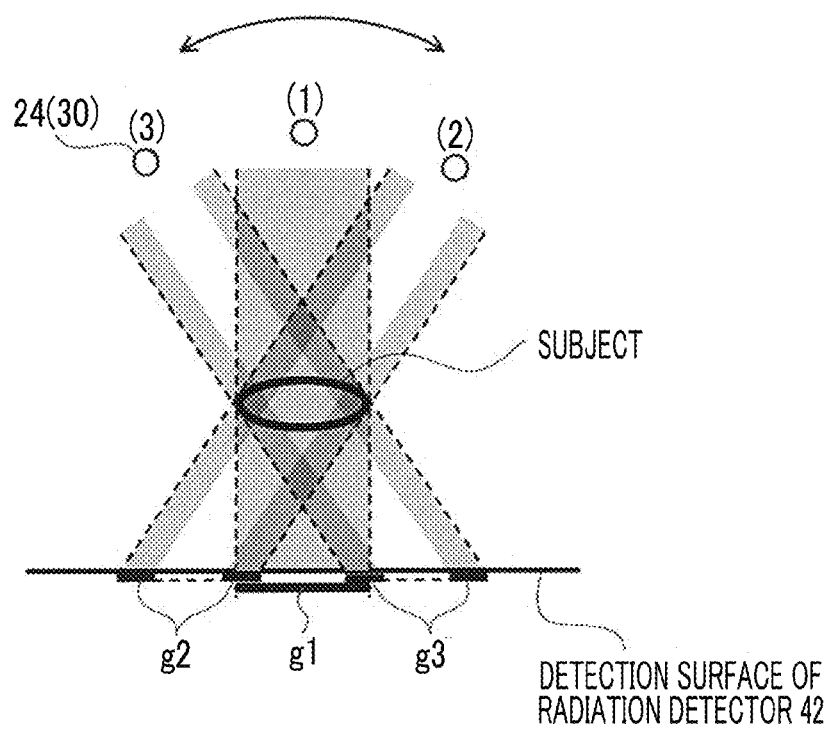
FIG. 9B is a front view schematically illustrating a case in which frequency processing that attenuates a low frequency component is performed for a projection image in which an incident angle is large.

The principle of the above-mentioned process will be described with reference to the schematic diagrams illustrated in FIGS. 9A and 9B. FIG. 9A is a front view schematically illustrating a case in which the original frequency processing is not performed for each projection image. FIG. 9B is a front view schematically illustrating a case in which the original frequency processing is performed for the projection image in which the incident angle is large.

FIGS. 9A and 9B illustrate an aspect in which the radiation emitting unit 24 is moved and emits radiation to the subject at three positions (1), (2), and (3) and three projection images are captured. (1) is a position where the incident angle is 0° and (2) and (3) are positions where the incident angle is equal to or greater than the first threshold value. In FIGS. 9A and 9B, the concentration of a portion in which the irradiation ranges of a plurality of radiations that are emitted from different directions overlap each other increases according to the overlap state. In the actual tomosynthesis imaging, cone beam radiation is emitted. However, here, for ease of understanding of the frequency processing, in the drawings, parallel radiations are emitted from each position.

As illustrated in FIG. 9A, when the subject is irradiated with radiation from the position (1), a subject image is projected onto an area G1 of the projection image. When the subject is irradiated with radiation from the position (2), a subject image is projected onto an area G2 of the projection image. When the subject is irradiated with radiation from the position (3), a subject image is projected onto an area G3 of the projection image. Therefore, in a case in which the tomographic image corresponding to the slice position where the subject is not originally present is reconstructed, an artifact is generated due to the areas G2 and G3.

As illustrated in FIG. 9B, when a low frequency component attenuation process is performed for the projection image which is captured by the irradiation of the subject with radiation from the position (2), the projection range of the subject image is limited to an area g2. Similarly, when the low frequency component attenuation process is performed for the projection image which is captured by the irradiation of the subject with radiation from the position (3), the projection range of the subject image is limited to an area g3. That is, as compared with the areas G2 and G3 in FIG. 9A, only the contour of the image of the subject remains and concentration in the image is attenuated. Therefore, even if the tomographic image corresponding to the slice position where the subject is not originally present is reconstructed from the projection images, the concentration of the artifact is reduced by the attenuation of the low frequency component. In addition, since the low frequency component attenuation process is not performed for the projection image which is captured by the irradiation of the subject with radiation from the position (1), a significant reduction in the concentration of the subject in the reconstructed tomographic image is suppressed.

In this embodiment, as an example of the frequency processing which attenuates the low frequency component relative to the high frequency component, the process of emphasizing the high frequency component is not performed and the process of attenuating the low frequency component is performed. However, the invention is not limited thereto. As the frequency processing, for example, the process of attenuating the low frequency component may not be performed and the process of emphasizing the high frequency component (hereinafter, referred to as a "high frequency component emphasis process") may be performed. In addition, as the frequency processing, both the process of attenuating the low frequency component and the process of emphasizing the high frequency component may be performed. For example, a process of attenuating both the low frequency component and the high frequency component may be performed. During the process, the degree of attenuation of the low frequency component may be D1 and the degree of attenuation of the high frequency component may be D2 that is less than D1. For example, a process of emphasizing both the low frequency component and the high frequency component may be performed. During the process, the degree of emphasis on the low frequency component may be D3 and the degree of emphasis on the high frequency component may be D4 that is more than D3.

In this embodiment, the frequency processing which attenuates the low frequency component relative to the high frequency component is performed for the projection image in which the incident angle is equal to or greater than the first threshold value. The first threshold value can be predetermined according to, for example, the interval at which the radiation emitting unit 24 (radiation source 30) is moved. In addition, the frequency processing unit 66 may perform frequency processing which attenuates each low frequency component for projection images other than the projection image in which the incident angle is the minimum. In this case, among the incident angles at which a plurality of projection images are captured, when the smallest incident angle is a1 and the second smallest incident angle is a2, the first threshold value can be set to be greater than the incident angle a1 and equal to or less than the incident angle a2. During tomosynthesis imaging, the position of the radiation source 30 is set in advance. Therefore, among a plurality of positions of the radiation source 30 during the tomosynthesis imaging, the position of the radiation source 30 where the incident angle is equal to or greater than the first threshold value may be set, instead of the first threshold value. In this case, the process of attenuating the low frequency component may be performed for the projection image obtained by irradiation with radiation from the set position.

Then, in Step 104, the CPU 52 controls the frequency processing unit 66 such that frequency processing (hereinafter, referred to as "first frequency processing") which increases the emphasis coefficient as the spatial frequency increases and increases the degree of emphasis is performed for the projection image (hereinafter, referred to as a "projection image to be processed") subjected to the above-mentioned process. The term "projection image to be processed" means both the projection image subjected to the original frequency processing in Step 102 and the projection image in which the incident angle is less than the first threshold value.

In the first frequency processing according to this embodiment, as the emphasis coefficient for the projection image subjected to the original frequency processing, the following value is used: a value for emphasizing the low frequency component attenuated by the original frequency processing in the range in which the degree of emphasis on the low frequency component is less than that before the attenuation.

As such, in this embodiment, as the first frequency processing, a process which increases the degree of emphasis as the spatial frequency is applied to all of the projection images to be processed. However, the invention is not limited thereto.

For example, as the first frequency processing, the following processes may be applied: a process which increases the degree of emphasis on a component other than the low frequency component attenuated in the original frequency processing as the spatial frequency increases; and a process which increases the degree of emphasis as the spatial frequency increases for only the projection image in which the incident angle is less than the first threshold value, that is, only the projection image which has not been subjected to the original frequency processing.

In addition, as the first frequency processing, a process may be applied which increases the degree of emphasis as the spatial frequency increases in a predetermined high frequency range. Here, the upper limit of the spatial frequency range is set in order to prevent an object (including noise generated when the projection image is generated) smaller than the object of interest, such as a calcification.

In Step 104, the frequency processing which increases the degree of emphasis as the spatial frequency increases is performed for the projection image to be processed, in order to prevent the object of interest with a relatively small size, such as a calcification, from being overlooked during radiographic interpretation. Therefore, as the emphasis coefficient used in this embodiment, the following value can be applied: a value at which the object of interest can be visually recognized when the resultant tomographic image obtained according to the size of the object of interest is interpreted and which is obtained in advance by, for example, an experiment using the actual radiography apparatus 10 or a computer simulation based on the design specifications of the radiography apparatus 10.

Then, in Step 106, the CPU 52 controls the tomographic image generation unit 68 such that the first tomographic image is reconstructed from the projection image subjected to the first frequency processing by the back projection method.

In a case in which the process of emphasizing the high frequency component is performed as the original frequency processing in Step 102, the first frequency processing is not necessarily performed. In this case, the process in Step 104 may not be performed. In this case, in Step 106, the first tomographic image is generated using the projection image to be processed which has been obtained in Step 102. In this case, it is preferable that the degree of emphasis on a high frequency component during the original frequency processing is the degree of emphasis that is obtained in advance as a value at which the object of interest can be visually recognized during radiographic interpretation.

Then, in Step 108, the CPU 52 outputs image information about the reconstructed first tomographic image (for example, to the image display instruction unit 62).

Then, in Step 110, the CPU 52 controls the frequency processing unit 66 such that frequency processing (hereinafter, referred to as "second frequency processing") which sets the emphasis coefficient to be less than that in the first frequency processing and increases the emphasis coefficient as the spatial frequency increases, thereby increasing the degree of emphasis is performed for the projection image to be processed.

In the second frequency processing according to this embodiment, a value that is a predetermined percent (for example, 50%) of the emphasis coefficient (hereinafter, referred to as a "first emphasis coefficient") applied in the first frequency processing is applied as the emphasis coefficient and the emphasis coefficient is less than that in the first frequency processing. However, the invention is not limited thereto. For example, a value obtained by subtracting a constant that is greater than 0 and less than 1 from the first emphasis coefficient may be applied as the emphasis coefficient.

In these aspects, different values (for example, larger values as the spatial frequency increases) may be applied as the percent and the constant in each predetermined spatial frequency range.

As such, in this embodiment, similarly to the first frequency processing, frequency processing which is performed for all of the projection images is applied as the second frequency processing. However, the invention is not limited thereto.

For example, as the second frequency processing, the following processes may be performed: a process which performs frequency processing for a component other than the low frequency component attenuated in the original frequency processing; and a process which performs frequency processing for only the projection image in which the incident angle is less than the first threshold value, that is, only the projection image which has not been subjected to the original frequency processing.

In addition, as the second frequency processing, a process may be applied which decreases the degree of emphasis to be less than that in the first frequency processing and increase the degree of emphasis as the spatial frequency increases, in a predetermined high frequency range.

In Step 110, the frequency processing which decreases the degree of emphasis to be less than that in the first frequency processing and increase the degree of emphasis as the spatial frequency increases is performed for the projection image to be processed, in order to reduce the generation of an artifact due to overemphasis.

Then, in Step 112, the CPU 52 controls the tomographic image generation unit 68 such that the second tomographic image is reconstructed from the projection image subjected to the second frequency processing by the back projection method.

Then, in Step 114, the CPU 52 controls the two-dimensional image generation unit 70 such that the above-mentioned projection process is performed to generate a composite two-dimensional image from the second tomographic image.

Figure 10:
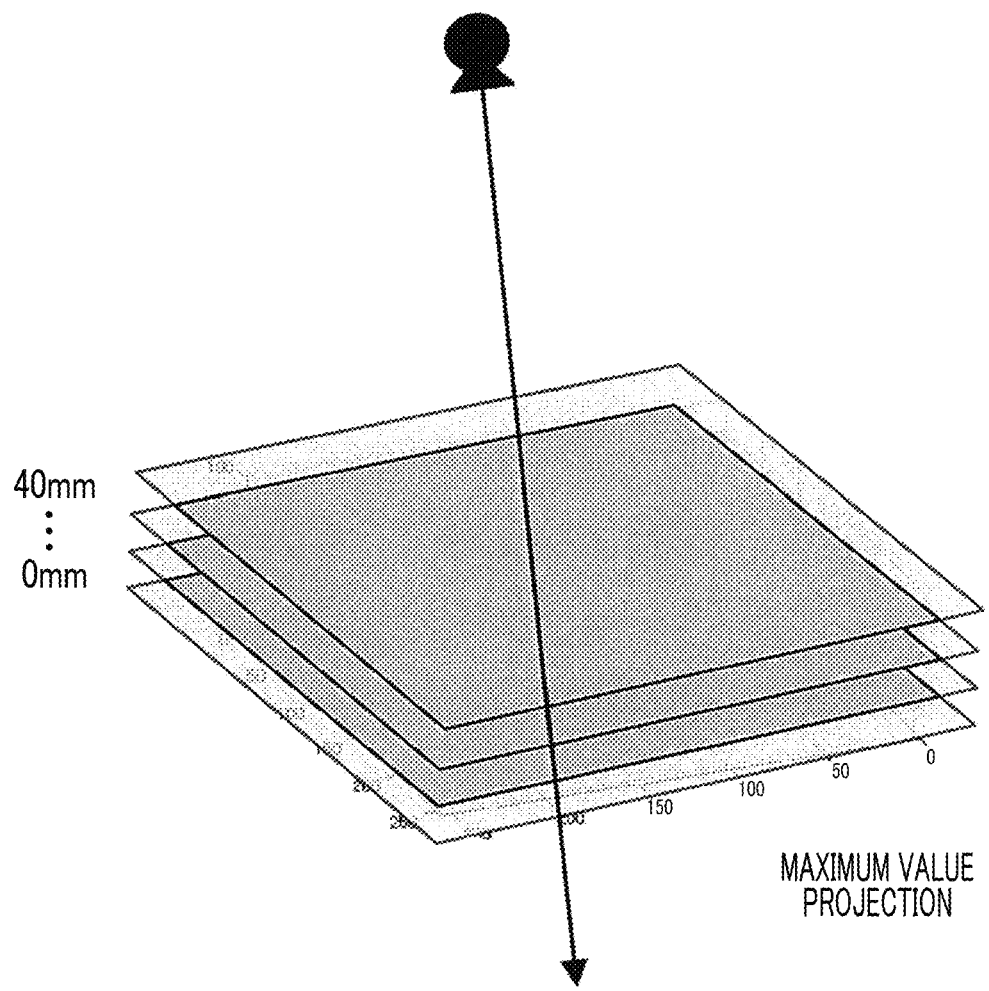
FIG. 10 is a front view schematically illustrating a maximum value projection process according to the embodiment.

Here, as illustrated in FIG. 10, first, the two-dimensional image generation unit 70 performs the projection process for a stacked image obtained by stacking a plurality of second tomographic images generated by the tomographic image generation unit 68 in an arbitrary viewpoint direction to select the maximum pixel value (brightness value) on a projection path. The two-dimensional image generation unit 70 performs this process for each pixel to generate the composite two-dimensional image. Alternatively, the two-dimensional image generation unit 70 may select the minimum pixel value on the projection path and generate the composite two-dimensional image. In addition, the two-dimensional image generation unit 70 may perform an addition process which adds the values of the pixels corresponding to each tomographic image in an arbitrary direction to generate the composite two-dimensional image. Furthermore, the composite two-dimensional image generation method disclosed in US2010/0135558A may be used. As such, commonly known methods may be used as the composite two-dimensional image generation method and the composite two-dimensional image generation method is not particularly limited.

Then, in Step 116, the CPU 52 outputs image information about the generated composite two-dimensional image (for example, to the image display instruction unit 62) and ends the first image generation processing program.

Figure 11:
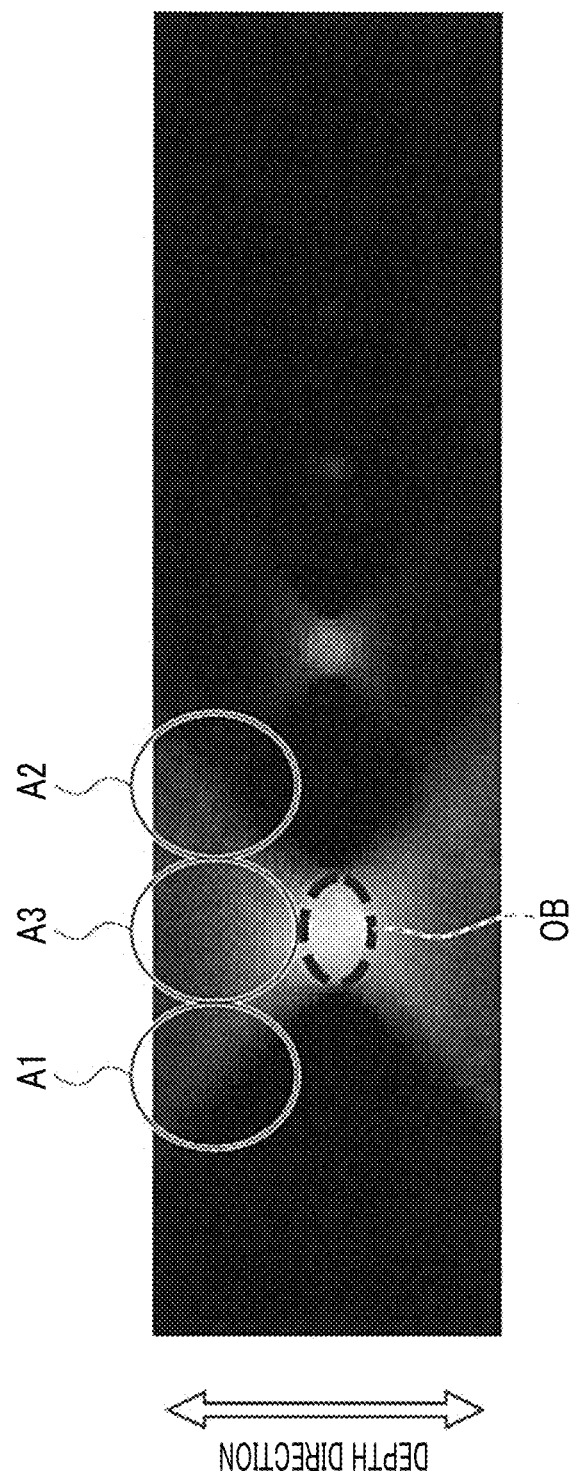
FIG. 11 is a diagram illustrating the influence of an artifact on a composite two-dimensional image.

However, as described above, the two-dimensional image generation unit 70 generates the composite two-dimensional image from the second tomographic image. Therefore, in some cases, the composite two-dimensional image is also affected by the artifact generated in the second tomographic image and image blur occurs. FIG. 11 is an example of a cross-sectional view illustrating a stacked image obtained by stacking the second tomographic images. When a region in which the object of interest is actually present is OB and, for example, an artifact is generated in the oblique direction of the region OB as represented by A1 and A2 in FIG. 11, the artifact causes the blurring of the composite two-dimensional image.

In contrast, in this embodiment, the frequency processing which attenuates a low frequency component relative to a high frequency component is performed for the projection image in which the incident angle is equal to or greater than the first threshold value and the tomographic image is reconstructed. Therefore, the tomographic image in which the artifact is inconspicuous is generated. As a result, an artifact is inconspicuous in the composite two-dimensional image generated from the tomographic image.

Since the process which attenuates a low frequency component relative to a high frequency component is not performed for the projection image in which the incident angle is less than the first threshold value, a reduction in the image concentration of the object of interest is suppressed. Therefore, for example, as represented by A3 in FIG. 11, an artifact remains a little in a region (a region immediately above the region OB) corresponding to the region OB at the slice position where the object of interest is not originally present. However, since the composite two-dimensional image is generated by the addition process or the projection process, the influence of the artifact represented by A3 in FIG. 11 on the blurring of the composite two-dimensional image is less than the influence of the artifacts represented by A1 and A2 in FIG. 11 on the blurring of the composite two-dimensional image.

In this embodiment, the frequency processing which increases the degree of emphasis as the spatial frequency increases is performed for the projection image to be processed to generate the first tomographic image and the frequency processing which decreases the degree of emphasis to be less than that in the first tomographic image and increases the degree of emphasis as the spatial frequency increases is performed for the projection image to be processed to generate the second tomographic image. In this way, the second tomographic image in which an artifact is less likely to be seen than that in the first tomographic image used for radiographic interpretation is generated. Therefore, an artifact is inconspicuous in the composite two-dimensional image generated from the second tomographic image, as compared to the case in which the composite two-dimensional image is generated from the first tomographic image.

That is, in this embodiment, the first tomographic image in which a relatively small object, such as a calcification, is emphasized is generated and the second tomographic image in which the artifact is less than that in the first tomographic image is generated. Therefore, a tomographic image which is suitable for both radiographic interpretation and the generation of the composite two-dimensional image is generated.

Figure 12:
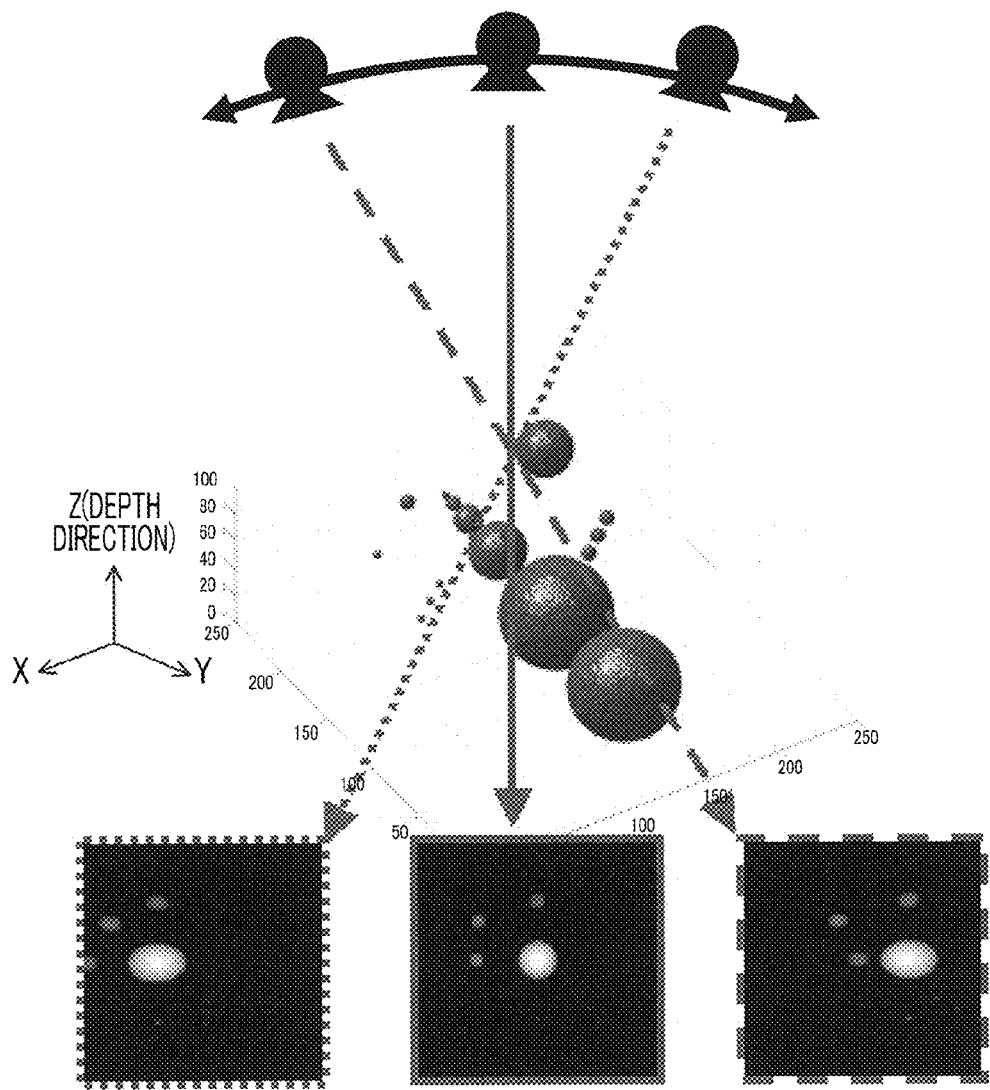
FIG. 12 is a diagram illustrating the generation state of a composite two-dimensional image according to the embodiment.
Figure 13A:
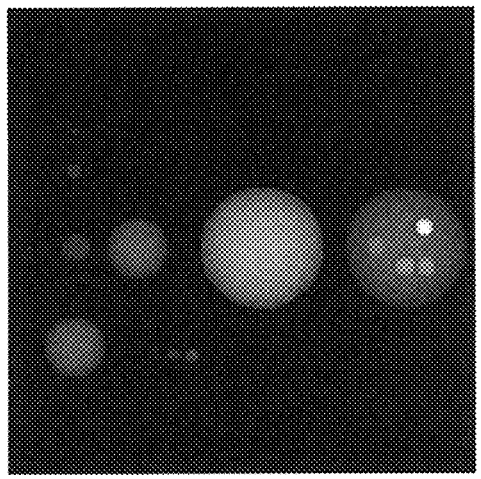
FIGS. 13A to 13C are diagrams illustrating an example of the generation result of the composite two-dimensional image according to the embodiment.
Figure 13B:
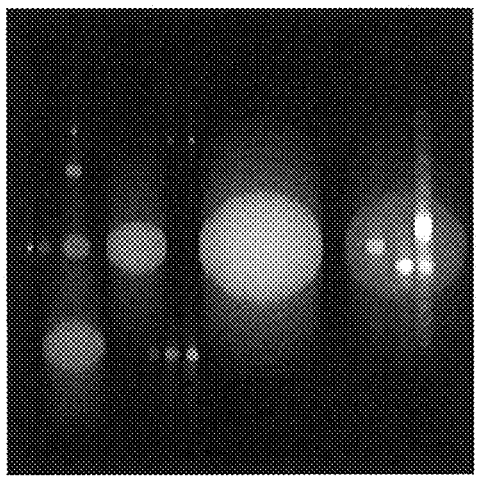
Figure 13C:
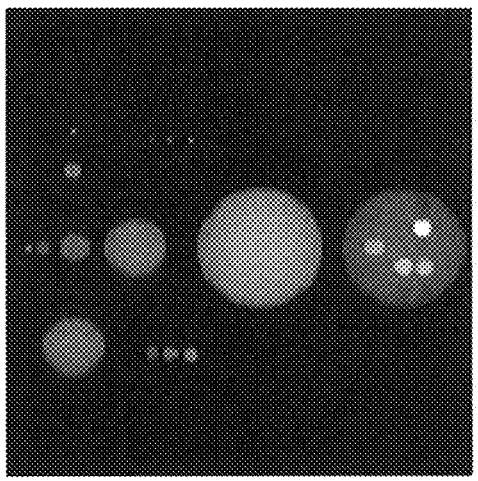

FIGS. 13A to 13C illustrate examples of the composite two-dimensional image which is generated in a case in which tomosynthesis imaging is performed for a plurality of objects with different sizes at different incident angles as illustrated in FIG. 12.

FIG. 13A illustrates an example of the two-dimensional image obtained by general radiography. FIG. 13B illustrates an example of the composite two-dimensional image which is generated using the tomographic image reconstructed from the projection image, without performing the original frequency processing and the second frequency processing. FIG. 13C illustrates an example of the composite two-dimensional image which is generated using the second tomographic image reconstructed from the projection image subjected to the original frequency processing and the second frequency processing. As illustrated in FIGS. 13A to 13C, in the composite two-dimensional image illustrated in FIG. 13C, the artifact is less than that in the composite two-dimensional image illustrated in FIG. 13B and a small object is more emphasized than that in the composite two-dimensional image illustrated in FIG. 13B.

In a case in which the addition process is performed to generate the composite two-dimensional image, the process may be performed while maintaining the balance between weights such that a change in the concentration of the entire image is matched with the actual concentration. For example, the weight of the second tomographic image corresponding to the slice position where the object of interest is present is greater than the weights of other second tomographic images.

As described above, in this embodiment, the image processing device 50 performs the original frequency processing corresponding to the incident angle for the projection image. Therefore, it is possible to suppress the generation of an artifact and a reduction in image concentration while maintaining the balance therebetween, as compared to a case in which frequency processing is collectively performed. In addition, in this embodiment, the image processing device 50 performs the first frequency processing for the projection image to be processed to reconstruct the first tomographic image and performs the second frequency processing for the projection image to be processed to reconstruct the second tomographic image. Therefore, it is possible to generate a tomographic image which is suitable for both radiographic interpretation and the generation of a composite two-dimensional image, as compared to a case in which the first frequency processing and the second frequency processing are not performed.

Second Embodiment

Next, a second embodiment of the invention will be described in detail. In this embodiment, since a radiography apparatus 10 has the same structure as the radiography apparatus 10 according to the first embodiment illustrated in FIGS. 1 to 3, the description thereof will not be repeated.

First, the structure of a radiography system 5 according to this embodiment will be described. The structure of the radiography system 5 according to this embodiment differs from the structure of the radiography system 5 (see FIG. 4) according to the first embodiment only in the functions of the frequency processing unit 66.

That is, in this embodiment, the frequency processing unit 66 performs the original frequency processing for the projection image, similarly to the first embodiment. In this embodiment, the frequency processing unit 66 does not perform first frequency processing and second frequency processing, which are the same as those in the first embodiment, for the projection image, but performs the first frequency processing and the second frequency processing for the tomographic image generated by the tomographic image generation unit 68.

Next, the operation of the radiography system 5 according to this embodiment will be described. Since the operations of the radiography apparatus 10 and the display device 80 according to this embodiment are the same as those in the first embodiment, the description thereof will not be repeated.

In this embodiment, the image processing device 50 performs the original frequency processing for the projection image and generates a tomographic image from the projection image. In addition, the image processing device 50 performs the first frequency processing for the generated tomographic image to generate a first tomographic image. Then, the image processing device 50 performs the second frequency processing for the generated tomographic image to generate a second tomographic image and generates a composite two-dimensional image from the second tomographic image.

Figure 14:
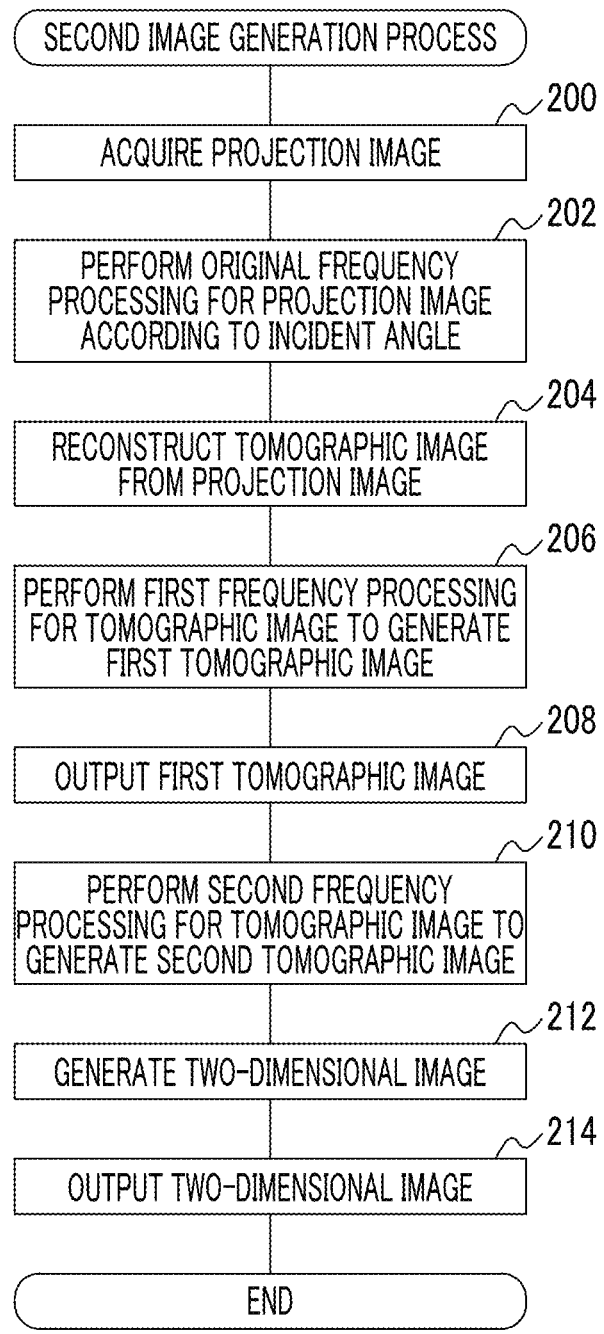
FIG. 14 is a flowchart illustrating the flow of the process of a second image generation processing program according to a second embodiment.
Figure 15:
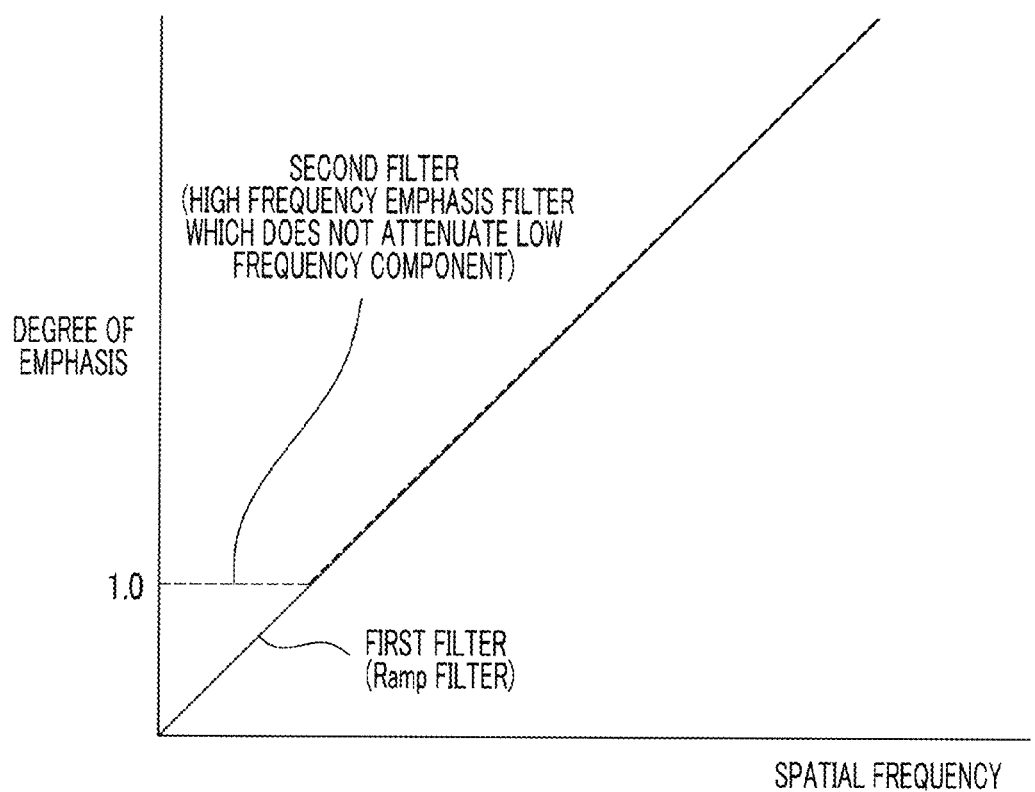
FIG. 15 is a graph illustrating an example of the characteristics of a first filter and a second filter.

Next, the operation of the image processing device 50 according to this embodiment will be described in detail with reference to the drawings. FIG. 14 is a flowchart illustrating the flow of the process of a second image generation processing program which is executed by the CPU 52 of the image processing device 50 according to this embodiment.

First, in Step 200 of FIG. 14, the CPU 52 acquires image information about the projection image, similarly to Step 100 in the process of the first image generation processing program according to the first embodiment. Then, in Step 202, the CPU 52 controls the frequency processing unit 66 such that the original frequency processing is performed for the projection image, similarly to Step 102 in the process of the first image generation processing program according to the first embodiment.

Then, in Step 204, the CPU 52 controls the tomographic image generation unit 68 such that a tomographic image (hereinafter, referred to as a "tomographic image to be processed") is reconstructed from the projection image to be processed which is the same as that in the first embodiment by the back projection method.

Then, in Step 206, the CPU 52 controls the frequency processing unit 66 such that the first frequency processing is performed for the tomographic image to be processed. In this embodiment, in the first frequency processing, the same emphasis coefficient as that in the first frequency processing according to the first embodiment is applied.

As such, in this embodiment, as the first frequency processing, a process which increases the degree of emphasis as the spatial frequency increases is applied to all of the tomographic images to be processed. However, the invention is not limited thereto.

For example, as the first frequency processing, a process may be applied which increases the degree of emphasis on a component other than the low frequency component attenuated in the original frequency processing as the spatial frequency increases.

In addition, as the first frequency processing, a process may be applied which increases the degree of emphasis as the spatial frequency increases in a predetermined high frequency range.

Then, in Step 208, the CPU 52 outputs the image information about the tomographic image (first tomographic image) subjected to the first frequency processing (for example, to the image display instruction unit 62), similarly to Step 108 in the process of the first image generation processing program according to the first embodiment.

In a case in which a process of emphasizing a high frequency component is performed as the original frequency processing in Step 202, the first frequency processing is not necessarily performed. In this case, the process in Step 206 may not be performed. In this case, in Step 208, the image information about the tomographic image to be processed, which has been obtained in Step 204, is output. In this case, it is preferable that the degree of emphasis on a high frequency component during the original frequency processing is obtained in advance as a value at which the object of interest can be visually recognized during radiographic interpretation.

Then, in Step 210, the CPU 52 controls the frequency processing unit 66 such that the second frequency processing is performed for the tomographic image to be processed. In this embodiment, in the second frequency processing, the same emphasis coefficient as that in the second frequency processing according to the first embodiment is applied.

As such, in this embodiment, a process which performs frequency processing for all of the tomographic images to be processed is applied as the second frequency processing. However, the invention is not limited thereto.

For example, as the second frequency processing, a process may be applied which performs frequency processing for a component other than the low frequency component attenuated in the original frequency processing.

In addition, as the second frequency processing, a process may be applied which decreases the degree of emphasis to be less than that in the first frequency processing and increases the degree of emphasis as the spatial frequency increases, in a predetermined high frequency range.

Then, in Step 212, the CPU 52 controls the two-dimensional image generation unit 70 such that a composite two-dimensional image is generated from the tomographic image (second tomographic image) subjected to the second frequency processing, similarly to Step 114 in the process of the first image generation processing program according to the first embodiment.

Then, in Step 214, the CPU 52 outputs image information about the generated composite two-dimensional image (for example, to the image display instruction unit 62), similarly to Step 116 in the process of the first image generation processing program according to the first embodiment, and ends the second image generation processing program.

As described above, in the radiography system 5 according to this embodiment, the radiography apparatus 10 captures a plurality of projection images, using tomosynthesis imaging. The image processing device 50 according to this embodiment acquires the plurality of captured projection images, stores the projection images in the storage unit 74, performs the original frequency processing corresponding to the incident angle for the acquired projection images, reconstructs the projection images to generate a tomographic image, and outputs the tomographic image. In addition, the image processing device 50 performs the first frequency processing for the reconstructed tomographic image to generate the first tomographic image. Then, the image processing device 50 performs the second frequency processing for the reconstructed tomographic image to generate the second tomographic image and generates a composite two-dimensional image from the second tomographic image.

As such, in this embodiment, the image processing device 50 performs the first frequency processing and the second frequency processing, which are performed for the projection image to be processed in the first embodiment, for the tomographic image to be processed. Therefore, according to the radiography system 5 of this embodiment, it is possible to obtain substantially the same effect as that in the first embodiment.

The invention has been described above using each embodiment. However, the technical scope of the invention is not limited to the scopes described in each of the above-described embodiments. Various modifications and changes in the above-described embodiments may be made without departing from the scope and spirit of the invention and the various modifications and changes are also included in the technical scope of the invention.

Each of the above-described embodiments does not limit the invention described in the claims and all of the combinations of the characteristics described in each embodiment are not essential to means for solving the problems in the invention. Each of the above-described embodiments includes the invention in various stages and various inventions are extracted by combinations of a plurality of components disclosed according to situations. In a case in which the same effect as described above is obtained even if some of the components described in each of the above-described embodiments are removed, a structure from which the components are removed is extracted as the invention.

For example, when performing the original frequency processing, the frequency processing unit 66 may increase the degree of relative attenuation of the low frequency component as the incident angle increases. For example, in a case in which a process of attenuating a low frequency component is performed for the projection image in which the incident angle is equal to or greater than the first threshold value, the frequency processing unit 66 may increase the degree of attenuation of the low frequency component as the incident angle increases. In addition, for example, in a case in which a process of emphasizing a high frequency component is performed for the projection image in which the incident angle is equal to or greater than the first threshold value, the frequency processing unit 66 may increase the degree of emphasis on the high frequency component as the incident angle increases. In this case, it is possible to suppress a reduction in the image concentration of the object of interest included in the tomographic image which is reconstructed from a plurality of projection images obtained by tomosynthesis imaging and the generation of an artifact while maintaining the balance therebetween.

The frequency processing unit 66 may be configured such that it performs frequency processing which emphasizes a low frequency component relative to a high frequency component for the projection image in which the incident angle is less than a second threshold value that is equal to or less than the first threshold value, as the original frequency processing corresponding to the incident angle which is performed by the frequency processing unit 66, in addition to the above-mentioned process. For example, the following process may be performed for the projection image in which the incident angle is less than the second threshold value: frequency processing which does not attenuate the high frequency component and emphasizes the low frequency component; frequency processing which does not emphasizes the low frequency component and attenuates the high frequency component; or frequency processing which emphasizes the low frequency component and attenuates the high frequency component. In this case, a reduction in the concentration of the object of interest relative to the concentration of the artifact is suppressed.

When performing the frequency processing which relatively emphasizes the low frequency component in the projection image in which the incident angle is less than the second threshold value, the frequency processing unit 66 may relatively increase the degree of emphasis on the low frequency component as the incident angle is reduced.

The frequency processing unit 66 may not set the first threshold value and the second threshold value and may perform frequency processing which increases the degree of emphasis as the incident angle increases and attenuates a low frequency component relative to a high frequency component in the spatial frequency of the projection image.

When performing the reconstruction, the tomographic image generation unit 68 may give a weight corresponding to the incident angle to the projection image and perform the reconstruction. For example, the tomographic image generation unit 68 may give weights such that the weight of the projection image in which the incident angle is equal to or greater than the first threshold value is less than the weight of the projection image in which the incident angle is less than the first threshold value and then perform the reconstruction. In this case, an artifact is inconspicuous. In addition, the tomographic image generation unit 68 may give a smaller weight to the projection image in which the incident angle is larger and perform the reconstruction.

Each of the frequency processing methods, that is, the original frequency processing, the first frequency processing, and the second frequency processing performed by the frequency processing unit 66 is not particularly limited. For example, convolution may be performed, using a filter in which weighting coefficients are one-dimensionally to two-dimensionally arranged, to perform each of the frequency processing methods.

In addition, each of the frequency processing methods may be performed by converting the image to be processed into information in a spatial frequency domain using Fourier transform, giving weights to each frequency component on the basis of the range of the frequency to be processed by each of the frequency processing methods and the emphasis coefficient, adding the weights, and returning the spatial frequency domain to a real space domain using inverse Fourier transform.

In addition, the multi-resolution analysis method disclosed in JP1994-301766A (JP-H06-301766A) may be used. Specifically, for example, an image in which a specific frequency component is attenuated or emphasized can be formed by performing a smoothing process to convert an image into images with a plurality of resolutions, calculating a difference image between the images for each resolution, giving a weighting coefficient to the difference image, and performing integration.

In a case in which an image is decomposed into a plurality of frequency components by, for example, Fourier transform or multi-resolution analysis and each of the frequency processing method is performed, the balance between the weights of each frequency component may be adjusted such that the generation of an artifact and a variation in the concentration of an image are suppressed. As such, since the balance between the weights can be freely (non-linearly) adjusted, the frequency processing which is performed for a plurality of decomposed frequency components can also be referred to as a non-linear filtering process.

Each of the above-mentioned frequency processing methods may be performed with the emphasis coefficient that depends on contrast. Specifically, in a case in which the non-linear filtering process is performed, the level of contrast for each frequency component can be determined and the weight of each frequency component can be changed depending on the level of the contrast. In a case in which there is an object with a high contrast (for example, a high absorber such as an artifact or a calcification), the degree of emphasis on a high frequency component may be reduced to suppress the generation of an artifact due to overemphasis. In addition, in a case in which there is an object with a low contrast, such as the mammary gland or a tumor mass, a low frequency component may be attenuated and a high frequency component may be positively emphasized so as to be conspicuous. As such, since frequency processing is performed depending on contrast, it is possible to reconstruct a tomographic image which facilitates diagnosis.

When the second tomographic image is generated, a reconstruction method using successive approximation may be used. Specifically, the number of iterative operations of the successive approximation in which the degree of emphasis is less than that in the first frequency is calculated. Then, the operation is repeatedly performed the calculated number of times by the successive approximation to reconstruct a tomographic image in which the artifact is reduced.

The original frequency processing which is performed in Step 102 of the process of the first image generation processing program according to the first embodiment is not indispensable. Therefore, the original frequency processing may not be performed. In this case, the image processing device 50 performs the first frequency processing for the projection image in Step 104 of the process of the first image generation processing program according to the first embodiment and performs the second frequency processing for the projection image in Step 110 of the process of the first image generation processing program according to the first embodiment.

Similarly, the original frequency processing which is performed in Step 202 of the process of the second image generation processing program according to the second embodiment is not indispensable. Therefore, the original frequency processing may not be performed. In this case, the image processing device 50 reconstructs a tomographic image from the projection image in Step 204 of the process of the second image generation processing program according to the second embodiment.

In each of the above-described embodiments, both the first tomographic image and the composite two-dimensional image are displayed on the display device 80. However, the invention is not limited thereto. Any one of the first tomographic image and the composite two-dimensional image may be displayed on the display device 80.

In each of the above-described embodiments, the first tomographic image and the second tomographic image are generated from the projection images stored in the storage unit 74 of the image processing device 50. However, the invention is not limited thereto. For example, the first tomographic image and the second tomographic image are generated from the projection images which are received from the outside through the network 49.

In each of the above-described embodiments, as the first frequency processing and the second frequency processing, the process which increases the degree of emphasis as the spatial frequency increases is performed for the image to be processed. However, the invention is not limited thereto. For example, in some cases, an object with a medium size between an object with a relatively large size, such as a calcification, and an object with a relatively large size, such as a tumor mass, is used as the object of interest. In this case, as the first frequency processing and the second frequency processing, a process may be performed which emphasizes a predetermined spatial frequency range, such as a spatial frequency range including the object with a medium size, relative to the other spatial frequency ranges.

In each of the above-described embodiments, the process which decreases the degree of emphasis to be less than that in the first frequency processing and emphasizes the image to be processed is performed as the second frequency processing. However, the invention is not limited thereto. For example, as the second frequency processing, a process may be performed which emphasizes a predetermined spatial frequency range, such as a spatial frequency range including the object with a medium size, such that the degree of emphasis on the predetermined spatial frequency range is more than that in the first frequency processing.

In the first embodiment, the first frequency processing and the second frequency processing are performed for the projection image. In the second embodiment, the first frequency processing and the second frequency processing are performed for the tomographic image. However, the invention is not limited thereto. For example, the first frequency processing and the second frequency processing may be performed for both the projection image and the tomographic image. In this case, preferably, the emphasis coefficients in the first frequency processing and the second frequency processing are adjusted such that the resultant first and second tomographic images are the same as the first and second tomographic images obtained by each of the above-mentioned embodiments.

In each of the above-mentioned embodiments, the image processing device is applied to generate the tomographic image from the projection image captured by mammography. However, the invention is not limited thereto. For example, the image processing device may be applied to generate a tomographic image from the projection image captured by other radiography apparatuses such as a so-called C-arm radiography apparatus which is rotated with the positional relationship between a radiation source and a radiation detector being fixed.

In addition, radiation which is used for tomosynthesis imaging is not particularly limited. For example, X-rays or gamma rays may be applied.

The structures of the radiography system 5, the radiography apparatus 10, the image processing device 50, and the display device 80 described in each embodiment are illustrative and can be changed according to situations, without departing from the scope and spirit of the invention.

In each of the above-mentioned embodiments, each of the frequency processing unit 66, the tomographic image generation unit 68, and the two-dimensional image generation unit 70 is implemented by hardware (for example, hardware formed by a general electronic circuit, an ASIC, or an FPGA). However, the units may be implemented by software, that is, the execution of a program by a computer, or a combination of hardware and software.

The flow of the process of each image generation processing program described in each embodiment (see FIGS. 5 and 14) is illustrative. Unnecessary steps may be removed, new steps may be added, or the order of the steps may be changed, without departing from the scope and spirit of the invention.

The disclosure of Japanese Patent Application No. 2013-205479 is incorporated herein by reference in its entirety.

All publications, patent applications, and technical standards mentioned in this specification are incorporated by reference in this specification to the same extent as if each individual publication, patent application, or technical standard was specifically and individually indicated to be incorporated by reference.

What is claimed is:

1. An image processing device comprising:
an acquisition unit for acquiring a plurality of projection images, which are captured at different incident angles by irradiating a subject that is positioned between a radiation detector and a radiation emitting unit and of which a tomographic image is to be generated with radiation at different incident angles with respect to a direction normal to a tomographic plane of the tomographic image, in a predetermined range while moving the radiation emitting unit;
a first tomographic image generation unit for generating a first tomographic image, which is emphasized according to a spatial frequency and is used for radiographic interpretation, on the basis of the projection images acquired by the acquisition unit;
a second tomographic image generation unit for generating a second tomographic image, which is emphasized according to the spatial frequency and on which the degree of emphasis is different from the degree of emphasis on the first tomographic image, on the basis of the projection images; and
a two-dimensional image generation unit for combining a plurality of second tomographic images generated by the second tomographic image generation unit to generate a composite two-dimensional image.

2. The image processing device according to claim 1, wherein the first tomographic image generation unit generates, as the first tomographic image, a tomographic image on which the degree of emphasis increases as the spatial frequency increases, on the basis of the projection images, and
wherein the second tomographic image generation unit generates, as the second tomographic image, a tomographic image which is emphasized less than the first tomographic image and on which the degree of emphasis increases as the spatial frequency increases, on the basis of the projection images.

3. The image processing device according to claim 2, wherein the first tomographic image generation unit performs a process which increases the degree of emphasis on the projection images as the spatial frequency increases, and generates the first tomographic image, via reconstruction using the projection images, and wherein the second tomographic image generation unit performs a process which sets the degree of emphasis on the projection images to be less than the degree of emphasis on the first tomographic image and increases the degree of emphasis on the projection images as the spatial frequency increases, and generates the second tomographic image, via reconstruction using the projection images.

4. The image processing device according to claim 2, wherein the first tomographic image generation unit generates a tomographic image, via reconstruction using the projection images, and performs a process which increases the degree of emphasis on the tomographic image as the spatial frequency increases to generate the first tomographic image, and wherein the second tomographic image generation unit generates a tomographic image, via reconstruction using the projection images, and performs a process which sets the degree of emphasis on the tomographic image to be less than the degree of emphasis on the first tomographic image and increases the degree of emphasis on the tomographic image as the spatial frequency increases to generate the second tomographic image.

5. The image processing device according to claim 1, wherein the first tomographic image generation unit and the second tomographic image generation unit determine a spatial frequency range in which the emphasis is performed, on the basis of the size of an object of interest during the radiographic interpretation.

6. The image processing device according to claim 1, further comprising:
a display unit for displaying at least one of the first tomographic image generated by the first tomographic image generation unit and the composite two-dimensional image generated by the two-dimensional image generation unit.

7. The image processing device according to claim 1, further comprising:
a processing unit for performing frequency processing which increases the degree of emphasis as the incident angle increases and attenuates a predetermined low frequency component of a spatial frequency of the projection images relative to a high frequency component having a higher spatial frequency than the low frequency component,
wherein the first tomographic image generation unit generates the first tomographic image on the basis of the projection images subjected to the frequency processing by the processing unit, and the second tomographic image generation unit generates the second tomographic image on the basis of the projection images subjected to the frequency processing by the processing unit.

8. The image processing device according to claim 7, wherein the processing unit performs, as the frequency processing, at least one of a process which attenuates the low frequency component of the projection image and a process which emphasizes the high frequency component of the projection image.

9. The image processing device according to claim 1, further comprising:
a processing unit for performing frequency processing which attenuates a predetermined low frequency component of a spatial frequency of a projection image in which the incident angle is equal to or greater than a predetermined first threshold value relative to a high frequency component having a higher spatial frequency than the low frequency component,
wherein the first tomographic image generation unit generates the first tomographic image on the basis of a projection image in which the incident angle is less than the predetermined first threshold value and the projection image subjected to the frequency processing by the processing unit, and
wherein the second tomographic image generation unit generates the second tomographic image on the basis of the projection image in which the incident angle is less than the predetermined first threshold value and the projection image subjected to the frequency processing by the processing unit.

10. The image processing device according to claim 9, wherein the processing unit performs, as the frequency processing, at least one of a process which attenuates the low frequency component of the projection image in which the incident angle is equal to or greater than the predetermined first threshold value or a process which emphasizes the high frequency component of the projection image in which the incident angle is equal to or greater than the predetermined first threshold value.

11. The image processing device according to claim 9, wherein, when performing the frequency processing, the processing unit increases the degree of relative attenuation of the low frequency component as the incident angle increases.

12. The image processing device according to claim 9, wherein at least one of the first tomographic image generation unit or the second tomographic image generation unit performs the generation on the basis of the projection image which is weighted according to the incident angle.

13. The image processing device according to claim 9, wherein the processing unit further performs frequency processing which emphasizes the low frequency component of a projection image, in which the incident angle is less than a second threshold value that is equal to or less than the first threshold value, relative to the high frequency component.

14. The image processing device according to claim 13, wherein, when performing the frequency processing which relatively emphasizes the low frequency component, the processing unit increases the degree of relative emphasis on the low frequency component as the incident angle decreases.

15. The image processing device according to claim 1, wherein the two-dimensional image generation unit performs a projection process for a stacked image, which is obtained by stacking the plurality of second tomographic images generated by the second tomographic image generation unit, in a predetermined direction or an addition process which adds values of corresponding pixels in the predetermined direction to generate the composite two-dimensional image.

16. A radiography system comprising:
a radiography apparatus that includes a radiation detector and a radiation emitting unit and irradiates a subject that is positioned between the radiation detector and the radiation emitting unit and of which a tomographic image is to be generated with radiation at different incident angles with respect to a direction normal to a tomographic plane of the tomographic image in a predetermined range while moving the radiation emitting unit to capture a plurality of projection images at different incident angles; and the image processing device according to claim 1, which generates a first tomographic image which is used for radiographic interpretation, a second tomographic image which is used to generate a composite two-dimensional image, and the composite two-dimensional image from the plurality of projection images captured by the radiography apparatus.

17. A non-transitory computer-readable storage medium storing an image processing program that causes a computer to execute:

an acquisition step of acquiring a plurality of projection images, which are captured at different incident angles by irradiating a subject that is positioned between a radiation detector and a radiation emitting unit and of which a tomographic image is to be generated with radiation at different incident angles with respect to a direction normal to a tomographic plane of the tomographic image, in a predetermined range while moving the radiation emitting unit;

a first tomographic image generation step of generating a first tomographic image which is emphasized according to a spatial frequency and is used for radiographic interpretation, on the basis of the projection images acquired by the acquisition step;

a second tomographic image generation step of generating a second tomographic image which is emphasized according to the spatial frequency and on which the degree of emphasis is different from the degree of emphasis on the first tomographic image, on the basis of the projection images; and a two-dimensional image generation step of combining a plurality of second tomographic images generated by the second tomographic image generation step to generate a composite two-dimensional image.

18. An image processing method comprising:

an acquisition step of acquiring a plurality of projection images, which are captured at different incident angles by irradiating a subject that is positioned between a radiation detector and a radiation emitting unit and of which a tomographic image is to be generated with radiation at different incident angles with respect to a direction normal to a tomographic plane of the tomographic image, in a predetermined range while moving the radiation emitting unit;

a first tomographic image generation step of generating a first tomographic image which is emphasized according to a spatial frequency and is used for radiographic interpretation, on the basis of the projection images acquired in the acquisition step;

a second tomographic image generation step of generating a second tomographic image which is emphasized according to the spatial frequency and on which the degree of emphasis is different from the degree of emphasis on the first tomographic image, on the basis of the projection images; and a two-dimensional image generation step of combining a plurality of second tomographic images generated in the second tomographic image generation step to generate a composite two-dimensional image.

* * * * *